(12) United States Patent
Sharpe et al.

(10) Patent No.: US 6,673,567 B2
(45) Date of Patent: Jan. 6, 2004

(54) METHOD OF DETERMINATION OF GENE FUNCTION

(75) Inventors: Pamela L. Sharpe, Newark, DE (US); Vasantha Nagarajan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/808,658

(22) Filed: Mar. 15, 2001

(65) Prior Publication Data

US 2003/0215799 A1 Nov. 20, 2003

Related U.S. Application Data

(60) Provisional application No. 60/191,561, filed on Mar. 23, 2000.

(51) Int. Cl.[7] .............................. C12Q 1/00; C12Q 1/68; C12Q 1/02; C12Q 1/04
(52) U.S. Cl. ............................. 435/29; 435/4; 435/6; 435/34
(58) Field of Search ............................. 435/29, 34, 6, 435/4

(56) References Cited

U.S. PATENT DOCUMENTS 5,869,239 A * 2/1999 Treco et al. ................... 435/6

FOREIGN PATENT DOCUMENTS

| WO | WO 9837205 A1 | 8/1998 |
|---|---|---|
| WO | WO 9950402 A1 | 10/1999 |
| WO | WO 0055346 A2 | 9/2000 |

OTHER PUBLICATIONS

Akerley et al. Systematic identification of essential genes by in vitro mariner mutagenesis vol. 95 pp. 8927–8932 Jul. 1998.*

Moore et al. Oncogenic potential of the ademovirus E4orf6 protein vol. 93 pp. 11295–11301, Oct. 1996.*

Hoang et al. A broad–host–range Flp–FRT recombination system for site–specific excision of chromosomally–located DNA sequences: application for isolation of unmarked Pseudomonas aeruginosa mutants Gene 212 1998 77–86.*

Gehring et al., Genomewide insertional mutagenesis in Streptomyces ceolicolor reveals additional genes involved in morphological differentiation, Department of Molecular and Cellular Biology, Harvard University, Aug. 15, 2000, Vol 97, No. 17.

Wong et al., Genetic footprinting with mariner–based transposition in Pseudomonas aeruginosa, Department of Microbiology and Molecular Genetics, Aug. 29, 2000, vol. 97, Mo. 18.

Pelicic et al., Mutagenesis of Neisseria meningitidis by In Vitro Transposition of Himar 1 mariner, Journal of Bacteriology, Oct. 2000, p 5391–5398.

Bolger, Methods Mol. Biol., Totowas, NJ 1998, 88, Protein Targeting Protocols, 101–131.

Kumar et al., Plant Biotechnol. Tokyo, 1998, 15(4), 159–165.

Gwinn et al., Journal of Bacteriology, 1997 Washington, D.C., Vol 179, No. 23, p. 7315–7320.

Reich et al., Journal of Bacteriology, 1999, Washington, D.C., vol. 181, No. 16 p. 4961–4968.

Happa et al., Genome Research 1999, 9:308–315.

Griffin et al., Nucleic Acid Research , 1999, 27(19) 3859–3865.

Lampe et al., Proc. Natl. Acad. Sci., (1999), 96:11428–11433.

Dyson, Methods Microbiol., 1999, 29 Genetic Methods for Diverse Prokaryotes, 133–167.

Stellwagen and Craig, The EMBO Journal, 1997, 16(22):6823–6834.

Haren et al., Annu. Rev. Microbiol., 1999, 53, 245–281.

Biery, Matthew et al., A simple in vitro Tn7–based transposition system with low target site selectivity for genome and gene analysis, Nucleic Acid Research, vol. 28, No. 5, Mar. 1, 2000, pp. 1067–1077, XP002210814.

Phillips, Gregory, New cloning vectors with temperature–sensitive replication, Plasmid, vol. 41, No. 1, Jan. 1999, pp. 78–81, XP002210815.

Happa et al., An efficient DNA sequencing strategy based on the bacteriophage Mu in vitro DNA transposition reaction, Genome Research, vol. 9, No. 3 Mar. 1999, pp. 308–315, XP002194598.

Devine et al., A transposon–based strategy for sequencing repetitive DNA in eucaryotic genomes, Genome Researach, vol. 7, 1997, pp. 551–563, XP002145187.

* cited by examiner

Primary Examiner—James Ketter
Assistant Examiner—Konstantina Katcheves

(57) ABSTRACT

The present method is useful for the identification of genes, ORF's and other nucleic acid molecules which are essential for the expression of a specific phenotype in microorganisms. The method employs In vitro transposition in conjunction with an chromosomal integration vector containing a specific gene or genetic element whose function is unknown. Subsequent transformation of a recombination proficient host with the vector and growth first under non-integrating conditions and then under integrating conditions, followed by a selection screen for either single or double crossover events results in transformants that may be subjected to phenotypic screens to determine gene function.

34 Claims, 7 Drawing Sheets

LB/Kanamycin

LB/Kanamycin/
Sucrose

LB/Kanamycin/
Chloramphenicol

Phenotype Master Plate

M9/Kanamycin

LB/Kanamycin

M9/Kanamycin

Phenol Red/Maltose

Phenol Red/Maltose

SEQUENCE LISTING

<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:primer
      sequence

<400> SEQUENCE: 1
gcaatgtaac atcagagatt ttgag                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:primer
      sequence

<400> SEQUENCE: 2
acctacaaca aagctctcat caacc                                          25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:primer
      sequence

<400> SEQUENCE: 3
ttggaattta atcgcggcct cgagc                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:primer sequence

<400> SEQUENCE: 4
gacggcggct tgttgaata aatcg                                          25

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:primer
      sequence

<400> SEQUENCE: 5
atccttaaaa actccatttc caccect                                       27

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:primer
      sequence

<400> SEQUENCE: 6
actttattgt catagtttag atctattttg                                    30

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:primer
      sequence

<400> SEQUENCE: 7
ccaaccagat aagtgaaatc tagttcc                                       27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer
      sequence

<400> SEQUENCE: 8
ccctctttaa tacgacgggc aattgc                                        26

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:primer
      sequence

<400> SEQUENCE: 9
gggtgcgcat gatcctctag agt                                           23

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:primer
      sequence -continued

```
<400> SEQUENCE: 10
taaattgcac tgaaatctag aaata                                              25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:primer
      sequence

<400> SEQUENCE: 11
tatttctaga tttcagtgca attta                                              25

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:primer
      sequence

<400> SEQUENCE: 12
actctagagg atcatgcgca ccc                                                23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:primer
      sequence

<400> SEQUENCE: 13
atgaaatcta acaatgcgct                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:primer
      sequence

<400> SEQUENCE: 14
attcaggtcg aggtggcccg                                                    20
```

METHOD OF DETERMINATION OF GENE FUNCTION

This application claims the benefit of U.S. Provisional Application No. 60/191,561, filed Mar. 23, 2000.

FIELD OF THE INVENTION

The invention relates to the field of molecular biology and microbiology. More specifically, a method has been developed whereby In vitro transposition is used to identify chromosomally integrated nucleic acid molecules having unknown function.

BACKGROUND OF THE INVENTION

With the advent of large-scale genome sequencing efforts, enormous amounts of sequence information is being made available to the research community on a daily basis. Genome sequencing efforts have been completed for the eukaryotes *Saccharomyces cerevisiae* and *Caenorhabditis elegans* and for several prokaryotes including *Esherichia coli, Mycoplasma gentalium, Bacillus subtilus, Thermotoga maritima, Methanococcus jannaschii*, including those of pharmaceutical interest. In spite of the volume of sequence data now available, only a small portion of the genes sequenced today from all these efforts have been functionally characterized.

The need to discover gene function has spawned a new area of research now referred to as "functional genomics". Functional genomics seeks to discover gene function with only nucleotide sequence information in hand. A variety of techniques and methods have been employed in this effort including the use of gene chips, bioinformatics, disease models, protein discovery and expression, and target validation. The ultimate goal of many of these efforts has been the development of high-throughput screens for genes of unknown function.

Techniques applied to elucidate gene function include identifying the interacting protein partner of a gene product as in the yeast 2-hybrid system (Bolger, G., *Methods Mol Biol.* (Totowa, N.J.) (1998), 88, (Protein Targeting Protocols), 101–131) and transposon tagging, which is useful in both microbial and eukaryotic genomes (Kumar et al., *Plant Biotechnol.* (Tokyo) (1998), 15(4), 159–165). The logarithmic increase in sequence data has driven the need for high-through-put (HTP) functional genomics screens. However, relatively few HTP methods have been developed to date. Traditional methods for the determination of gene function still remain the basis of the functional genomics effort.

Classically, the first and most basic analysis for any gene is the creation of a null mutation to assess the phenotype of the organism when the gene of interest is rendered nonfunctional. These null mutations are often produced by gene disruption (also called gene knockout or gene replacement) using gene disruption vectors produced by recombinant DNA techniques. Upon transformation into the organism the DNA construct with disrupted gene integrates at the resident location in the genome by homologous recombination and replaces the functional copy of the gene with the nonfunctional gene disruption vector. Gene disruption vectors are constructed from a genomic clone containing the gene of interest.

The above methods have worked well for disruption of genes in a range of organisms but have several inherent limitations, including being limited to knowledge of restriction sites, the unpredictable effects of co-suppression or gene silencing as well as being time consuming and labor intensive. More rapid methods that are adaptable to high throughput screening are needed for the functional analysis of gene function.

Transposons have proven to be invaluable genetic tools for molecular geneticists. Several uses of transposon include mutagenesis for gene identification, reporter libraries for analysis of gene expression, DNA sequencing for relative gene positioning on genetic maps, etc. Until recently, however, all of these applications involved the use of in vivo transposition reactions. However, the commercialization of several In vitro transposition reactions for DNA sequencing and mutagenesis could lead to the replacement of these more traditional in vivo methodologies with more efficient biochemical procedures.

The use of In vitro transposition for the mutagenesis of specific genes was first reported by Gwinn et al. (*Journal of Bacteriology*, (1997) (Washington, D.C.), vol. 179, no. 23, p. 7315–7320). In their work, the genomic DNA from the naturally transformable microorganism (*Haemophilus influenzae*) was mutagenized using the Tn7 In vitro transposition system. DNA sequencing using primers that hybridize to the end of the transposon identified mutations in the genes resulting in a reduced expression of constitutive competence genes.

Reich et al. (*Journal of Bacteriology*, (1999) (Washington, D.C.), vol. 181, no. 16, p. 4961–4968) used the Ty1-based transposition system (Primer Island) to scan the entire *Haemophilus influenzae* genome for essential genes. The putative essential genes were identified by two methods—mutation exclusion and zero time analysis. Mutational exclusion involves the identification of open reading frames that do not contain transposon insertions. Zero time analysis involves the monitoring the growth of individual cells after transformations over time; cells containing transposon insertions into-essential genes will be lost over time.

However, to date the use of In vitro transposition for making chromosomal mutations has been limited to the naturally transformable microorganisms (e.g., *Haemophilus influenzae*). Since most microorganisms are not naturally transformable, methods for making random chromosomal mutations in all microorganisms in a high-throughput manner is needed. Because the above two systems use linear DNA in the transformations, single-crossover events cannot be obtained. Thus, the above systems are not useful to making mutations in essential genes that are involved in cell survival. Another limitation is that the above systems cannot be used to determine the functions of unknown genes on a genomic scale.

The present invention solved the problems by providing a method to make random mutations in genomic scale and screen for essential genes that are responsible for the specific phenotype.

SUMMARY OF THE INVENTION

The present invention provides a method for the identification of an essential gene responsible for the presence of a specific phenotype in a recombination proficient microorganism comprising:

a) contacting In vitro:
   (i) a transposable element comprising at least one first genetic marker;
   (ii) a transposase for the insertion of the transposable element into the essential gene; and
   (iii) target DNA containing the essential gene, said gene having a homolog in the genome of the recombination proficient microorganism;

under suitable conditions whereby the transposable element inserts within the essential gene to form a transposon disrupted gene;
b) cloning the transposon-disrupted gene into a suitable vector to form a chromosomal integration vector, said vector comprising at least one second genetic marker;
c) transforming a recombination proficient microorganism which is not naturally transformable with the chromosomal integration vector of step (b) to create transformants;
d) selecting the transformants of step (c) under conditions whereby no chromosomal integration occurs between the chromosomal integration vector and the genome of the transformant, by identifying transformants expressing the first genetic marker;
e) culturing the identified transformants of step (d) under conditions whereby chromosomal integration occurs between the chromosomal integration vector and the genome of the transformant;
f) selecting transformants of step (e) which express either the first genetic marker or both the first and second genetic markers by which transformants having undergone either a single or double crossover event are identified;
g) screening the transformants of step (f) which have undergone either a single or double crossover event, for the presence of a specific phenotype wherein the transformants which are positive for the specific phenotype contain a transposon disrupted gene; and
h) isolating the transposon disrupted gene from the transformant of step (g) which is positive for the specific phenotype.

In one embodiment step (d) of the above described method is optionally deleted.

Additionally the method may comprise using a temperature sensitive chromosomal integration vector which will integrate into the host genome at a non-permissive temperature. Thus the invention provides a method for the identification of an essential gene responsible for the cell growth under any condition in a recombination proficient microorganism comprising:
a) contacting In vitro:
   (i) a transposable element comprising at least one marker;
   (ii) a transposase for the insertion of the transposable element into the essential gene; and
   (iii) target DNA containing the essential gene, said gene having a homolog in the genome of the recombination proficient microorganism;
   under suitable conditions whereby the transposable element inserts within the essential gene to form a transposon disrupted gene;
b) cloning the transposon disrupted gene into a temperature sensitive vector containing a second genetic marker to form a temperature sensitive chromosomal integration vector;
c) transforming a recombination proficient microorganism, which is not naturally transformable, with the temperature sensitive chromosomal integration vector of step (b) to create transformants;
d) culturing the transformants of step (c) at a permissive temperature whereby no chromosomal integration occurs between the chromosomal integration vector and the genome of the transformant;
e) identifying transformants of step (d) expressing the marker;
f) culturing the identified transformants of step (e) at non-permissive temperatures whereby chromosomal integration occurs between the chromosomal integration vector and the genome of the transformant;
g) selecting transformants of step (e) which did not grow at step (f) after chromosomal integration between the chromosomal integration vector and the genome of the transformant and which contain a transposon disrupted gene; and
h) isolating the transposon disrupted gene from the transformant of step (g) which is responsible for cell growth under any condition.

In one embodiment a third genetic marker may be used. Thus the invention additionally provides a method for the identification of an essential gene responsible for the presence of a specific phenotype in a recombination proficient microorganism comprising:
a) contacting In vitro:
   (i) a transposable element comprising at least one first marker;
   (ii) a transposase for the insertion of the transposable element into the essential gene; and
   (iii) target DNA containing the essential gene, said gene having a homolog in the genome of the recombination proficient microorganism;
   under suitable conditions whereby the transposable element inserts within the essential gene to form a transposon disrupted gene;
b) cloning the transposon disrupted gene into a suitable vector to form a chromosomal integration vector, said vector comprising at least one second marker and at least one third marker;
c) transforming a recombination proficient microorganism which, is not naturally transformable, with the chromosomal integration vector of step (b) to create transformants;
d) selecting the transformants of step (c) under conditions whereby no chromosomal integration occurs between the chromosomal integration vector and the genome of the transformant, by identifying transformants expressing the first marker;
e) culturing the identified transformants of step (d) under conditions whereby chromosomal integration occurs between the chromosomal integration vector and the genome of the transformant;
f) selecting transformants of step (e) which express either the first marker alone, the first and second markers alone, or the first, second and third markers, by which transformants having undergone either a single or double crossover event are identified;
g) screening the transformants of step (f) which have undergone either a single or double crossover event, for the presence of a specific phenotype wherein the transformants which are positive for the specific phenotype contain a transposon disrupted gene; and
h) isolating the transposon disrupted gene from the transformant of step (g) having the specific phenotype.

Genetic markers used in the present method may be selectable or screenable and may incorporate genes useful for the construction of positive selection vectors, such as the sacB gene of Bacillus. In a preferred embodiment the first and second genetic markers are different.

BRIEF DESCRIPTION OF THE FIGURES AND SEQUENCES

FIG. 1 describes the screen for integration events (single- or double-crossover events) when using positive selection (sacB gene). Single-crossover is a marked with 'circle' and the double-cross over is marked with 'X' on the Phenotype master plate.

FIG. 2 describes a confirmation method for single- and double-crossover events. Single-crossover is a marked with 'circle' and the double-cross over is marked with 'X' on the Phenotype master plate.

FIG. 3 describes the screen for integration events (single- or double-crossover events) when using negative selection (Ampicillin resistance gene).

Figure 6:
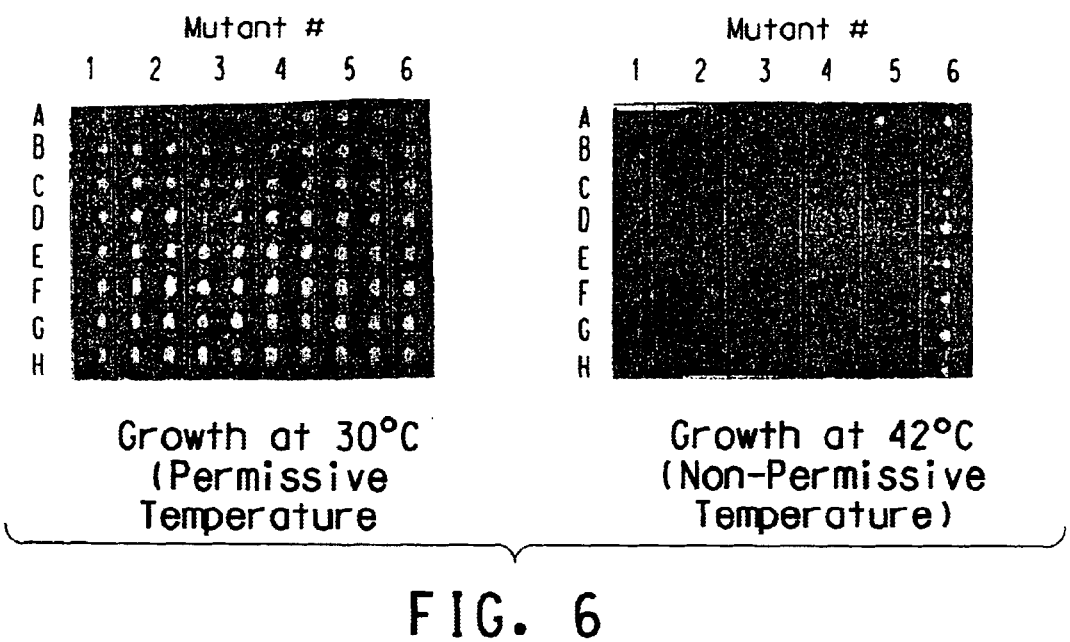

FIG. 6 describes the screening method for identifying genes essential for growth using temperature sensitive vectors.

Figure 7:
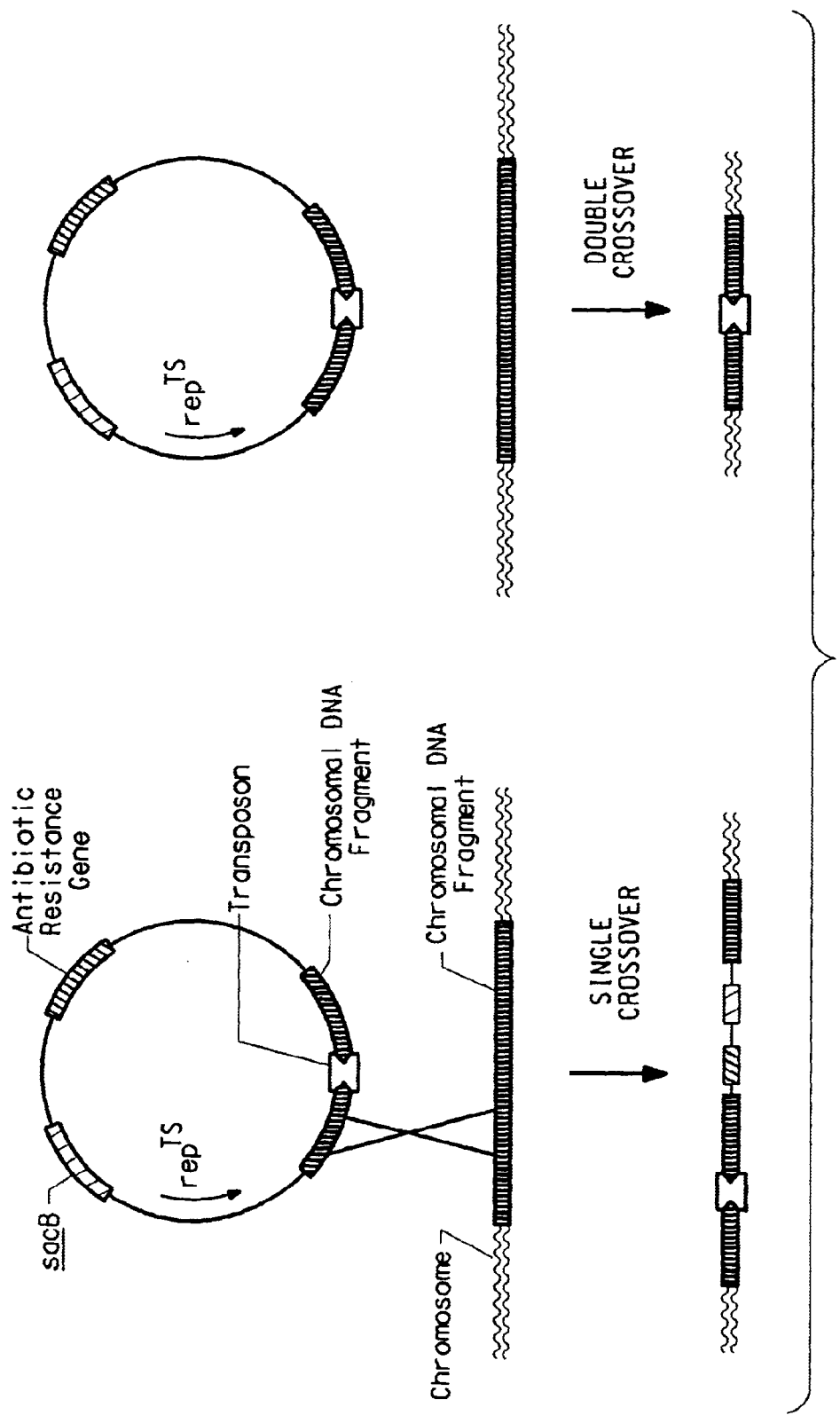

FIG. 7 is the schematic diagram of single- and double-crossover events.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1–14 are the DNA sequencing primer sequences used in the present invention.

The invention can be more fully understood from the following detailed description and the accompanying sequence descriptions, which form a part of this application.

DETAILED DESCRIPTION OF THE INVENTION

The present method is useful for the identification of genes or other nucleic acid molecules whose function has not been determined. The method is particularly useful in uncovering the function of genes responsible for a specific phenotype under various conditions. For example, the identification of genes that confer resistance to chemical compounds, i.e. herbicides, insecticides, pesticides etc., can be rapidly identified using the present invention. The present method can also speed-up the identification of novel metabolic pathways from environmental microorganisms that carry out interesting chemistry. Thus, the present invention will help facilitate the engineering of optimal hosts to be used in the production molecules from microorganisms. The present invention can also be used to identify genes that are essential under all growth conditions and therefore may serve as potential drug target by the pharmaceutical industry.

The present method is useful for the identification of genes, ORF's and other nucleic acid molecules, which are essential for the expression of a specific phenotype in microorganisms. The method employs In vitro transposition in conjunction with a chromosomal integration vector containing a specific gene or genetic element whose function is unknown. Subsequent transformation of a recombination proficient host with a chromosomal integration vector and growth first under non-integrating conditions and then under integrating conditions, followed by a selection screen for either single or double crossover events. The discovery of genetic function can be determined by further screening the host containing the integrated transposon-disrupted gene for the identification of a phenotype.

In this disclosure, a number of terms and abbreviations are used. The following definitions are provided.

The terms "transposon" and "transposable element" are used interchangeably and mean a region of nucleic acid that is capable of moving from one position to another within DNA molecule where this movement is catalyzed by the element itself.

The terms "single crossover event" and "plasmid integration" are used interchangeably and mean the incorporation of a chromosomal integration vector into the genome of host via homologous recombination between regions of homology between DNA present within the chromosomal integration vector and the host's chromosomal DNA. (see FIG. 7)

The terms "double crossover event", "allelic exchange" and "gene replacement" are used interchangeably and mean the homologous recombination between a DNA region within the chromosomal integration vector and a region within the chromosome that results in the replacement of the functional chromosomal gene with a disrupted non-functional copy of the same gene or gene homolog (see FIG. 7).

The term "In vitro transposition" means a biochemical reaction that is initiated outside the cell that catalyzes the movement of a transposable element from one site into different site within a DNA molecule.

The term "in vivo transposition" means a biochemical reaction that takes place within the cell that catalyzes the mobilization of a transposon from of site to another within the genome of the host.

The term "transposase" means a protein that catalyses the chemical steps i.e., breakage and joining, of a transposition reaction.

The term "genetic marker" means a phenotypic trait that can be visualized under special conditions.

The term "SacB" means a Bacillus encoded protein that catalyses the conversion of sucrose into Levan, which is toxic in gram negative microorganisms. The term "sacB" means a gene that encodes "SacB" protein.

The term "essential gene" or "essential nucleic acid molecule" means the genes that are necessary to display a specific characteristic in the cell. For an example, "essential gene" for growth or environmental conditions means that cells are not viable if the gene is disrupted or if cells are grown under a specified set of conditions that require the gene expression. The "essential gene" used in the context of a phenotype means that cells do not display the specific phenotype if the essential gene is disrupted or prevented from expression. Essential genes are contained within "target DNA". "Target DNA" may be any DNA that contains the essential gene. It may be, for example, restricted chromosomal or genomic DNA or may be a short gene fragment.

The term "chromosomal integration vector" means an extra-chromosomal vector that is capable of integrating into the host's genome through homologous recombination.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "temperature-sensitive plasmid" means a vector that can replicate autonomously at certain temperatures (permissive temperature) but is unable to replicate at other temperatures (non-permissive temperature).

The term "gene disruption" means a process in which the coding region of a gene is interrupted by the transposition of a transposable element into that gene. A "transposon disrupted gene" means any gene having a transposable element inserted therein.

The term "chromosomal integration" means that a chromosomal integration vector becomes congruent with the chromosome of a microorganism through recombination between homologous DNA regions on the chromosomal integration vector and within the chromosome.

The term "recombination proficient" means that a microorganism is capable of integrating extra-chromosomal DNA into its genome via homologous recombination.

The term "not naturally transformable" refers to a recombination proficient microorganism which will not naturally take up foreign DNA.

"Open reading frame" is abbreviated ORF.

As used herein, an "nucleic acid molecule" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure. "Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention may be used for the determination of gene function. The present invention uses In vitro transposition to insert a transposon into an essential gene contained within a target DNA. The essential gene may be essential for any type of detectable phenotype. Additionally the essential gene must either be derived from the host, or have a homolog in the host genome. After the transposon has been inserted into the target DNA, it is cloned into a vector. The transposon is associated with a unique genetic marker which distinguishes it from the marker on the vector. The chromosomal integration vector containing the disrupted essential gene is then use to transform a recombination proficient host which is not naturally transformable. Integration by the vector into the host genome results in either single or double cross over integration events which may be screened for on the basis of the transposon associated marker or the vector associated marker. Once transformants are identified to have integration events, screens that are designed to detect specific phenotypes may determine gene function.

In vitro Transposition

The present method employs a method of In vitro transposition to disrupt the essential gene of interest. In vitro transposition involves the use of a transposable element in combination with a transposase enzyme. When the transposable element or transposon is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element.

Kits for In vitro transposition are commercially available (see for example The Primer Island Transposition Kit, available from Perkin Elmer Applied Biosystems, Branchburg, N.J., based upon the yeast Ty1 element (including the AT2 transposon); The Genome Priming System, available from New England Biolabs, Beverly, Mass., based upon the bacterial transposon Tn7; and the EZ::TN Transposon Insertion Systems, available from Epicentre Technologies, Madison, Wis., based upon the Tn5 bacterial transposable element).

Although not available commercially, several other In vitro transposition reactions have been reported in the literature. A DNA sequencing tool was developed based on the bacteriophage Mu In vitro transposition reaction.(Haapa et. al., *Genome Research* (1999), 9:308–315). Similarly, a tool for DNA sequencing and mutagenesis was developed based on the bacterial transposon Tn552 In vitro transposition system (Griffin et. al., *Nucleic Acid Research* (1999), 27(19) 3859–3865). The mariner transposable element Himar1 also has an In vitro transposition reaction used for mutagenesis and DNA sequencing (Lampe et. al., *Proc. Natl. Acad. Sci.*, (1999), 96:11428–11433).

Thus, transposons suitable in the present invention include but are not limited to those based upon the yeast Ty1 element, those based upon the bacterial transposon Tn7, the EZ::TN, those based on the bacteriophage Mu, those based on the bacterial transposon Tn552, and the mariner transposable element Himar1. A number of transposons and methods of identifying and isolating transposons are reviewed by Dyson, Paul J, *Methods Microbiol.* (1999), 29(Genetic Methods for Diverse Prokaryotes), 133–167, incorporated herein by reference. Although these specific transposon systems have been developed for use in In vitro systems, it is contemplated that many of the transposon systems, currently only available for In vivo transposition, may be modified and developed for In vitro work. With the appropriate development and characterization these In vivo transposon systems will also be suitable within the context of the present invention.

Although any commercially available In vitro transposition system can be used as a mutagenizing tool, the Tn7-based In vitro transposition system (New England Biolabs, Beverly, Mass.) is preferred for making chromosomal mutations. In addition to being able to customize the Tn7-based element with the appropriate selectable genetic marker for the microorganism under study, the insertion of the Tn7-based transposon into any DNA target molecule renders that molecule "immune" to further insertions by the Tn7-based element (Stellwagen and Craig, *The EMBO Journal*, (1997), 16(22):6823–6834). It is extremely important that only one gene is disrupted in each mutant, which permits the high-throughput assignment of gene function to be straightforward.

It is most suitable if the transposable element of the present invention were associated with a selectable or screenable genetic marker. The genetic marker is used to identify transformants having the transposon disrupted gene or gene fragment. The genetic marker may be associated with the transposon in any fashion, however it is particularly suitable if the genetic marker is located between the ends of the transposon. Most common are antibiotic resistance markers (i.e. ampicillin-resistances, Kanamycin-resistance, tetracycline-resistance etc.). Also suitable are genetic markers encoding metal resistance, substrate-utilization, and genes encoding fluorescent and bioluminescent proteins (e.g. green fluorescent proteins, Lux genes.), as well as, lacz gfp, cat, galK, inaZ, luc, luxAB, bgaB, nptII, phoA, uidA and xcylE.

Markers may be used singly or in association with other agents to identify allelic exchange. For example, tetracycline can also be used in combination with detergents for the detection of cells that have lost the non-homologous region of the chromosomal integration vector (Maloy and Nunn, *Journal of Bacteriology*, (1981), 145(2):1110–1112).

The transposase can exist in two different forms. The transposase for Tn5 and Ty1 are made up of a single protein, as are most transposases, and is responsible for target site selection as well as the chemical reactions. In contrast, the Tn7 transposase is made up of several proteins. One set of Tn7 proteins is responsible for selecting the target sites and the other set of Tn7 proteins is needed to carry out the chemical steps of the reaction. A variety of transposases are known in the literature. For a discussion of transposase use and function see Haren et al., *Annu. Rev. Microbiol.* (1999), 53, 245–281.

Chromosomal Integration Vectors

Another aspect of the present invention is the use of a chromosomal integration vector carrying a transposon disrupted gene for integration into a recombination proficient host cell genome. Vectors or cassettes useful for the transformation of suitable host cells are well known in the art. Typically, the vector or cassette contains sequences directing transcription and translation of the relevant gene, a selectable or screenable genetic marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a host.

Initiation control regions or promoters, which are useful to drive expression of the essential genes in the desired host cell are numerous and familiar to those skilled in the art. Virtually any promoter capable of driving these genes is suitable for the present invention. Preferred promoters for present invention are but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, ara, tet, trp, $1P_L$, $1P_R$, T7, tac, and trc (useful for expression in *Escherichia coli*) as well as the amy, apr, npr promoters and various phage promoters useful for expression in Bacillus.

Termination control regions may also be derived from various genes native to the preferred hosts. Optionally, a termination site may be unnecessary, however, it is most preferred if included.

In a preferred embodiment, a vector that remains autonomous under one set of conditions and integrates under another set of conditions is particularly useful. Temperature sensitive vectors meet these criteria. Thus, one preferred vector is the one that is temperature-sensitive for replication. These vectors are able to replicate as a plasmid at one set of temperatures (permissive temperature) but fail to replicate at another set of temperatures (non-permissive temperature).

The chromosomal integration vector may be constructed in a variety of ways. Typically chromosomal DNA (or target DNA) is subjected to restriction enzyme digestion and then to In vitro transposition. The chromosomal DNA fragments will be either isolated from the host organism, or will have homologs in the host organism.

The transposon is not targeted to any specific portion of the DNA, the transposon inserts randomly throughtout DNA. Some insertions take place into genes that are essential for the phenotype under scrutiny. Alternatively, insertion can be targeted by using isolated genes or gene fragments that are known to contain all or a portion of the target DNA. This approach is referred as "targeted insertion". In either case a library of chromosomal DNA fragments containing insertions is then cloned into the vector. It is the homology between the transposon-tagged chromosomal DNA fragment within the chromosomal integration vector and the same gene or gene homolog within the host's genome that facilitates the integration of the non-functional gene copy into the chromosome of the host.

Essential genes of the present invention are contained within the chromosomal DNA fragments and may be any gene or coding region that expresses a detectable phenotype. Typically the essential gene will be present in the host organism. However, the present method is applicable to situations where the essential gene is only a homolog of one in the host genome. In some instances the essential gene may be essential for cell growth under any conditions. In this case, disruption of this gene will lead to cell death. More typically the essential gene will encode an enzyme necessary for growth under specific conditions, i.e. amino acid synthesis. Examples of specific phenotypes that may be screened for in the present method include but are not limited to, metabolic capacity (e.g. carbon source requirement, auxotroph requirement, amino acid requirement, nitrogen source requirement, and purine requirement); resistance to inorganic chemicals (e.g. acid, arsenate, azide, heavy metals, and peroxide); resistance to organic and biological chemicals (e.g. herbicides, fungicides, bactericidal agents, bacteriostatic agents, antibiotics, acridine, actinomycin, amino purine, amino phenylalanine, colicin, ethanol, fluoroacetate, mitomycin C, and nalidixic acid); resistance to biological agents (e.g. phages); resistance to physical extremes (e.g. temperature, pH, osmotolerance and radiation); enzymatic function (e.g. assays for protease, phosphatase, coagulase, urease, catalase, etc.); fatty acid composition; degradation; and hydrolysis. The phenotypes amenable to detection by the present invention are numerous and a full review may be found in, Robert LaRossa: *Escherichia coli and Salmonella: Cellular and Molecular Biology* (1996) ASM press p. 2527–2587).

A multiplicity of screens are available and known in the art to detect the above mentioned phenotypes. For examples see Manual of *Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). Where a screen is positive it indicates that the specific phenotype being screened for is blocked or inhibited.

In a preferred embodiment a selectable or screenable genetic marker is located on the vector. This genetic marker is in addition to the marker that is associated with the transposon and will be detected by a different method. The marker used on the vector may be of the same type as those used with the transposable element, or may be different. Antibiotic markers are typically used. Additionally genes causing lethality under certain conditions may also be used as efficient genetic markers. Such genes may be used to create a "suicide vector" or "positive selection vector". A suicide vector is capable of replicating in one host but not in another. In the host where the suicide vector cannot replicate, the transposon-tagged chromosomal DNA fragment within the vector can replace the host's functional gene through homologous recombination. An example of the suicide vector approach is a vector containing the *Bacillus amyloliquefaciens* levansucrase gene, sacB as a marker. Vectors expressing the sacB gene in the presence of sucrose cause the sucrose to be converted to levan, which is toxic to most gram negative bacteria. The sacB gene is only one example of similar genes that may be used as markers in the construction chromosomal integration vectors of the present invention having positive selection attributes. For a review of other genes and the construction of positive selection vectors generally see Maniatis, supra; Alexeyev, Mikhail F., *BioTechniques* (1999), 26(5), 824,826,828; Matin et al., *Anal. Biochem.* (2000), 278(1), 46–51;and Bramucci et al., WO 9716558.

Recombination Proficient Microorganism

One aspect of the present invention is the transformation of a recombination proficient host microorganism by the chromosomal integration vector where double and single crossover events may be screened. Introduction of the chromosomal integration vector into such a host cell may be accomplished by known procedures such as by transformation, e.g., using calcium-permeabilized cells, electroporation, transduction, or by transfection using a recombinant phage virus. (Maniatis supra)

The method described here can be applied to virtually any microorganism that can take-up foreign DNA and is recombination proficient, i.e., can exchange extra-chromosomal DNA homologous to a region within the host's genome.

Although any bacteria satisfying these criteria is a potential candidate for this method, this method primarily targets microorganisms that are not naturally transformable. Hence, the present method requires a non-replicating chromosomal integration vector as an intermediate in the process. Several authors (Lee et al., *Applied and Environmental Microbiology* (1999), 65(5):1883–1890) have described methods identifying essential genes from naturally transformable bacteria, such as Haemophilus and Staphylococcus. Since there are significantly more bacteria that cannot take-up DNA naturally (not naturally transformable), the present invention has a much broader application.

Microbial hosts that are particularly suitable in the present invention are those species which cannot naturally take up DNA and are selected from, but not limited to, the genera, Pseudomonas, Bacillus, Bacteriodes, Vibrio, Yersinia, Clostridium, Mycobacterium, Mycoplasma, Coryynebacterium, Escherichia, Salmonella, Shigella, Rhodococcus, Methanococcus, Micrococcus, Arthrobacter, Listeria, Klebsiella, Aeromonas, Streptomyces and Xanthomonas. Similarly the present method may be applied to eukaryotic microorganisms such as yeast or fungi. Examples of eukaryotic host strains useful in the present invention include but are not limited to fungal or yeast species such as Aspergillus, Trichoderma, Saccharomyces, Pichia, Candida, and Hansenula, which are not naturally transformable.

In some instances, where vector construction and amplification are difficult in a particular host, it may be necessary to manipulate the vector in an alternate host, more amenable to genetic techniques. The types of alternate host chosen will be apparent to the skilled person, based on the knowledge of the genetic systems of the recombination proficient host. In the present invention, for example, where Rhodococcus, was the recombination proficient host, a recA *E. coli* mutant was useful for vector construction and amplification.

Screening Methods

Methods of screening in microbiology are discussed at length in Brock, supra. In one preferred embodiment, cells that have undergone a single crossover-event, (i.e., the entire integration vector becomes congruent with the chromosome), are selected by plating onto rich medium that permits phenotypic selection. The gene expresses the selectable marker is present within the transposon. The cells are subsequently plated onto rich medium and selected on the basis of two different selectable markers. In addition to the transposon's selectable markers, a second phenotypic marker must be present within the chromosomal integration vector's DNA. Cells that are able to grow on medium containing only the selecting agent that screens for the presence of the transposon, but not on medium that also screens for the presence of the chromosomal integration vector's selectable marker have undergone allelic exchange (double-crossover event). In contrast, cells that are capable of growing on medium containing both selecting agents have undergone a single-crossover event and merely integrated the entire chromosomal integration DNA molecule (vector plus the transposon-tagged chromosomal DNA fragment) into the host's genome.

There are also conditions in which cells that have undergone double-crossover events (allelic exchange) can be selected for directly by applying positive selection pressure. For example, when cells are transformed with a chromosomal integration vector that also contain the Bacillus sacB gene, only cells in which the disrupted non-functional gene replaces the functional chromosomal gene will be able to grow on rich medium supplemented with sucrose. SacB converts sucrose into levan, which is toxic to most gram-negative bacteria.

The direct selection of double-crossover events also can be accomplished by having the gene that confers resistance to tetracycline on the vector portion of the non-replicating circular DNA. Tetracycline is a bacteriostatic antibiotic. It does not kill the cells but instead inhibit their growth. It has been demonstrated in the literature that tetracycline-resistant cells are hypersensitive to lipophilic chelating agents, such as, fusaric acid (Maloy and Nunn, *Journal of Bacteriology*, (1981), 145(2): 1110–1112). Therefore, screening colonies on medium containing fusaric acid can monitor double-crossover events.

Description of the Preferred Embodiments

The key features in developing a method that permits the rapid generation of chromosomal mutations and the high-throughput assignment of gene function are (1) the use of In vitro transposition for the generation of random insertional mutations throughout the chromosomal DNA isolated from microbes of interest, (2) the use of a chromosomal integration vector for the construction of a library of transposon-tagged chromosomal DNA fragments (for microorganisms that are not naturally transformable), (3) the use of microbes that are capable of receiving foreign DNA (through transformation, electroporation or conjugation) and (4) the use of microbes that are recombination proficient.

Transposon mutagenized chromosomal DNA is ligated into a chromosomal integration vector. This library of transposon-tagged mutants is introduced into a recombination competent host which facilitates the exchange of the mutated and wild-type alleles. Since the selectable marker on the vector is different from the selectable marker present on the transposon, single-crossover and double-crossover events can easily be distinguished from each other by plating on the appropriate medium. This collection of transposon-tagged mutants may be simultaneously subjected to high-throughput screens that permit the assignment of gene function to unknown ORFs. The screening of the mutants occur in a semi-automated fashion.

Figure 1:
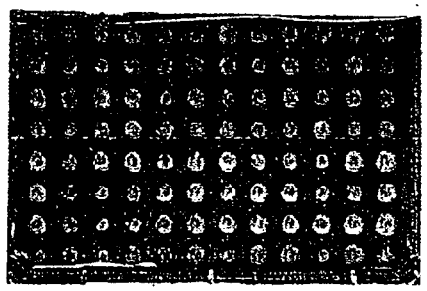
Figure 1:
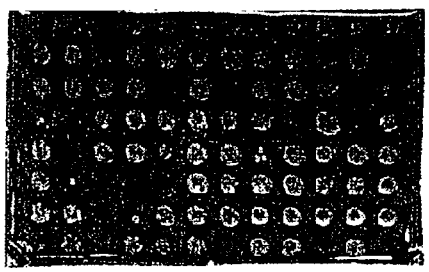
Figure 1:
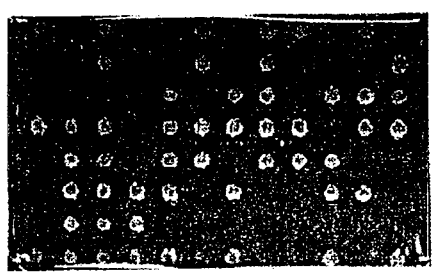
Figure 1:
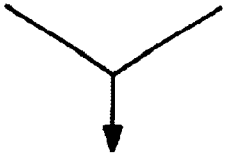
Figure 2:
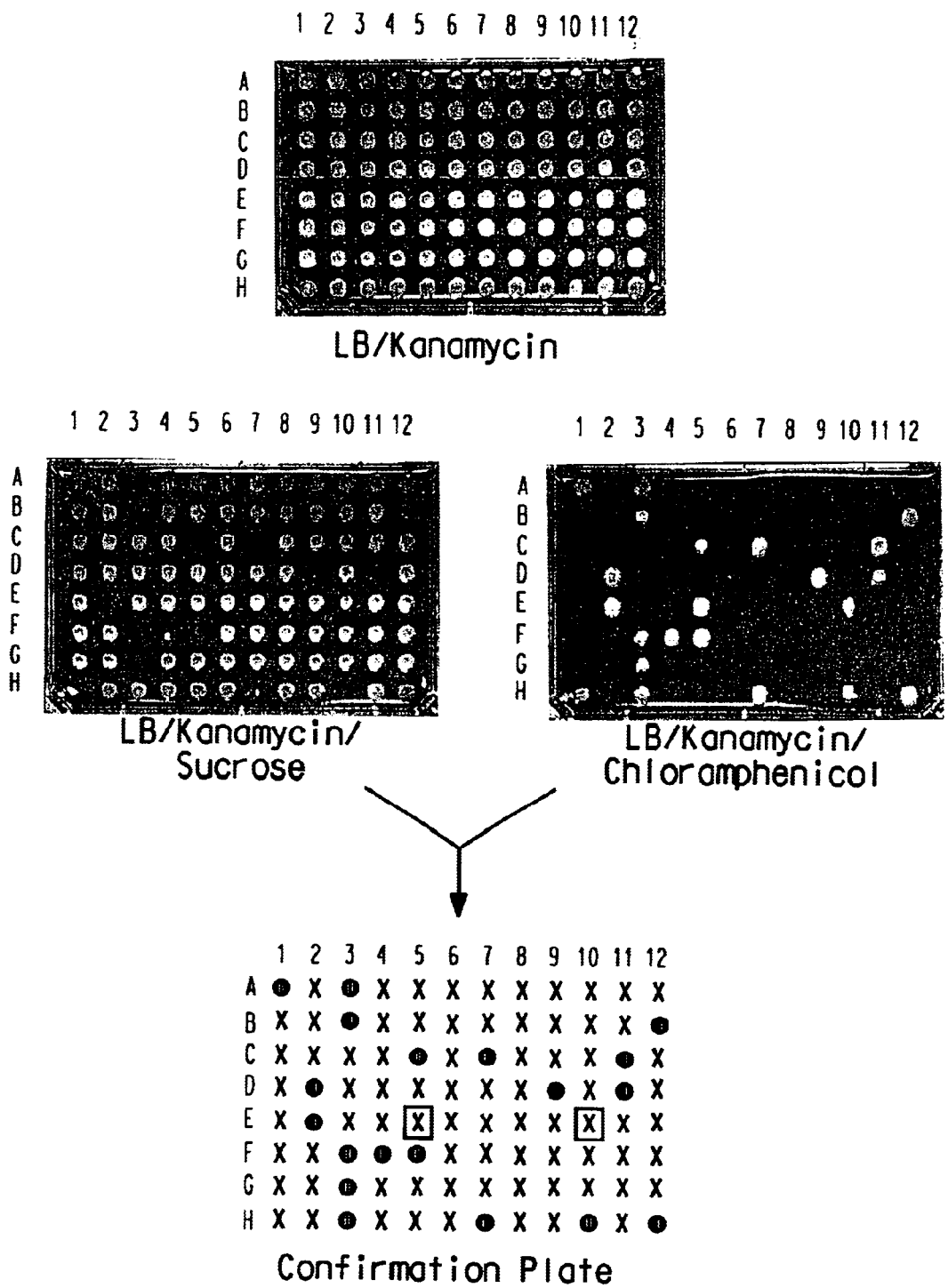

In one embodiment, *E. coli* strain W3110 was transformed with DNA that had been randomly mutagenized using an In vitro transposition technique. The transposon donor plasmid in the reaction carried a kanamycin resistant gene between the ends of the transposable element. The temperature-sensitive vector carried a chloramphenicol gene and the npr-sacB gene that permitted the positive selection of double crossover events at the non-permissive temperature. After transformation, cells were plated onto kanamycin agar plates which permitted the growth of all cells receiving mutagenized *E. coli* W3110 DNA. Then cells were plated in a 96-well format. The cells were screened for integration events (single- or double-crossover) by their ability to grow on the kanamycin-sucrose agar plates and kanamycin-chloramphenicol plates. Of all the cells that could grow on the kanamycin plates (integration and single-crossover), only a portion could grow on the kanamycin-chloramphenicol agar plates and kanamycin-sucrose agar plates (FIGS. 1 and 2). Growth on the kanamycin-sucrose agar plates and lack of growth on the chloramphenicol containing plates indicated that the transposon-disrupted gene replaced the functional chromosomal copy of the gene and the vector sequence with chloramphenicol resistant gene and sacB gene sequences were lost (integration and double-crossover). Where cells were viable with a single-crossover but not with a double-crossover, it indicated that the disrupted gene(s) were essential for growth.

Figure 3:
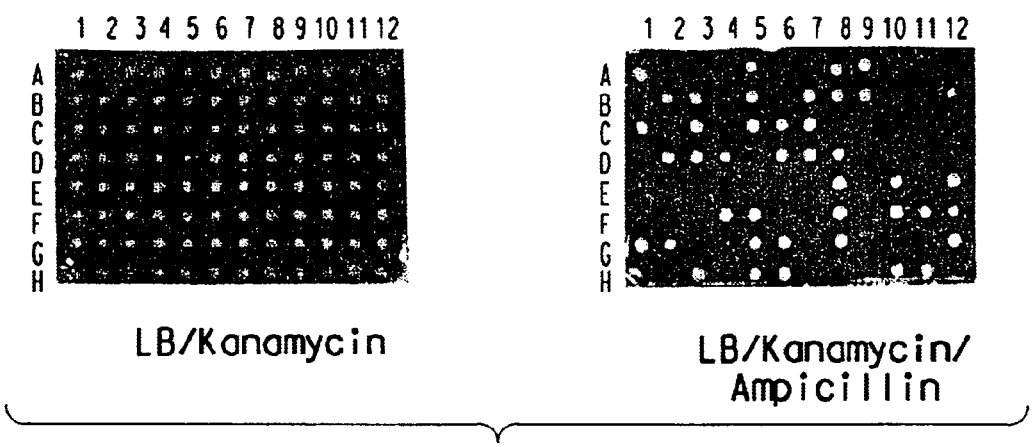

In an alternative embodiment, *E. coli* strain W3110 was transformed with DNA that had been randomly mutagenized using an In vitro transposition technique. The transposon donor plasmid in the reaction carried a kanamycin resistant gene between the ends of the transposable element. After transformation, cells were screened for integration events (single- or double-crossover) by their ability to grow on the kanamycin plates and kanamycin-ampicillin plates. Of all the cells that could grow on the kanamycin plates (integration and single-crossover), only a portion could grow on the kanamycin-ampicillin plates. Lack of growth on the ampicillin containing plates indicated that the transposon-disrupted gene replaced the functional chromosomal copy of the gene and the vector sequence with ampicillin resistant gene sequences were lost (integration and double-crossover) (FIG. 3). Where cells were viable with a single-crossover but not with a double-crossover, it indicated that the disrupted gene(s) were essential for growth.

Figure 4A:
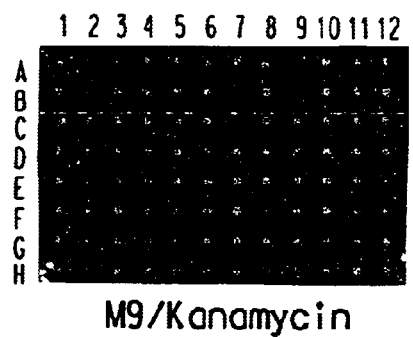
FIG. 4a illustrates a screening method for identifying auxotrophic mutants using a minimal nutrient (M9)growth medium, showing the colonies that can grow in M9+kanamycin medium.
Figure 4B:
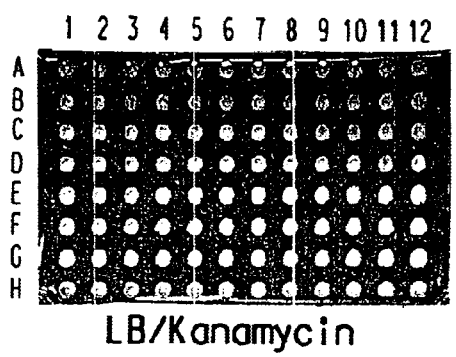
FIG. 4b illustrates a screening method for identifying auxotrophic mutants using a minimal nutrient (M9)growth medium, showing a duplicate culture to that of FIG. 4a, that can grow in enriched medium (LB)+kanamycin but cannot grow in minimal media (M9)+kanamycin shown in well B8 and F7.
Figure 4B:
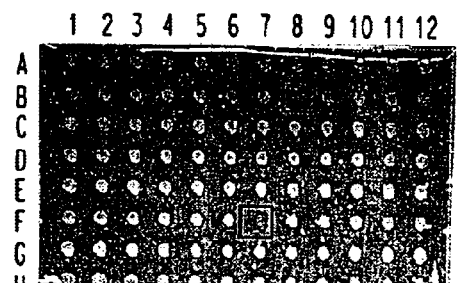

All cells in 96 wells from each "Phenotype master plate" were evaluated to determine their phenotype by inoculating in the medium (liquid or solid) containing various substrate of interest. In order to determine whether transposon has disrupted any genes for synthesizing amino acids that are essential for growth on minimal medium (M9), duplicate plates were made, one with LB medium with kanamycin and the other with M9 with kanamycin (FIGS. 4a and 4b). Cells that could grow on LB with kanamycin but not on M9 with kanamycin were considered auxotrophic mutants.

Figure 5A:
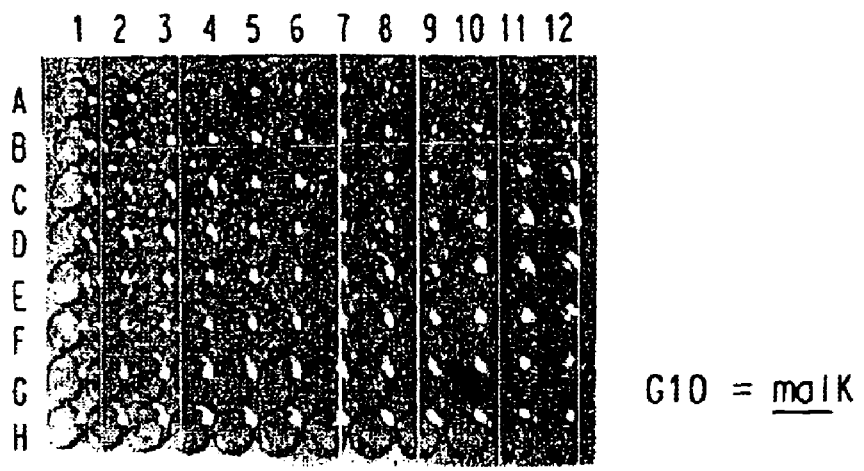
FIG. 5a illustrates a Phenol Red based colorimetric screen for identifying maltose fermentation mutations having lost the ability to produce acid when grown in the presence of maltose.

Colorimetric assays were used to screen the transposon-tagged mutants or phenotypes. For example, Phenol Red broth supplemented with maltose was used to screen for mutants that had lost their ability to produce acid when grown in the presence of maltose. Cells containing a transposon insertion into malK gene was identified. It is known that malK gene product is involved in transporting maltose into cell (FIG. 5a).

Figure 5B:
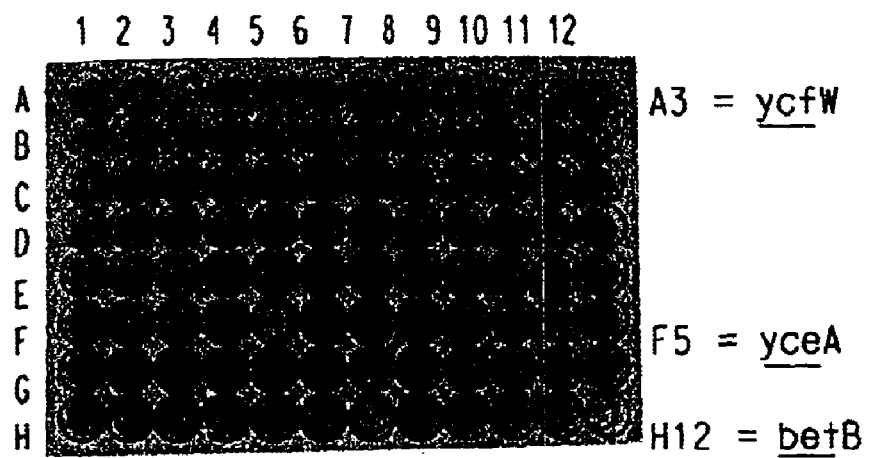
FIG. 5b illustrates colorimetric screen for identifying fermentation mutations which have acquired the ability to produce acid when grown in the presence of sucrose.

Colorimetric assay were used to screen for mutants that acquired a new phenotype. For example, some transposon-tagged mutants acquired the ability to produce acid when grown in the presence of sucrose (FIG. 5b). The location of the insertion was determined to be into genes of unknown function (ycfW, yceA), and betB, a gene that is involved in synthesis of glycine betaine from choline.

Some genes are essential for growth under all conditions. For this type of essential gene, cells that have undergone double-crossover cannot be obtained because loss of that gene function results in cell death. To identify these genes, positive selection using sacB gene in the vector were used. Since the product of sacB gene is lethal to cell, only the cells that have undergone double-crossover and lost the vector sequence can survive (Table 1).

Another way to identify the genes essential for growth is to use dominant lethals. In this case, cells with a single-crossover event cannot be isolated because the presence of one disrupted copy of the gene is lethal to the cell. To facilitate screening temperature sensitive vectors were used and grown at permissive temperatures, permitting all cells to grow. When the temperature was shifted to non-permissive temperature, some cells were unable to grow. (FIG. 6), and the crossover events were identified. Since the transposon sequence is known, the sequence of disrupted gene can be determined using PCR.

Although the present embodiments were practiced according to traditional screening methods, it is contemplated that screening the library of transposon-tagged mutants may take place in a high-throughput manner. Additionally the process may be automated such that hundreds to thousands of mutants can be analyzed simultaneously. The essential genes that are required for different growth conditions can be identified by screening for specific phenotypes, for example auxotrophic mutation, or using temperature sensitive vector that allows cell growth in permissive temperature but not in non-permissive temperature.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified. The meaning of abbreviations is as follows: "g" means microliters, "mL" means milliliters, "L" means liters.

Example 1

Construction of Genomic Library in Chromosomal Integration Vector

Isolation of Chromosomal DNA

A "seed" culture of *E. coli* strain W3110 was prepared by inoculating an isolated colony into 5 mL of LB broth. The culture was grown overnight with shaking at 37° C. The following day a 1:1000 dilution of the seed culture was made into fresh LB broth and the culture was grown to an OD600 equal to 0.7–0.8. The cells were pelleted and resuspended into 2.5 mL of 10 mM Tris-EDTA. A hundred microliter of lysozyme (5mg/mL) was added to the cells. Following a 15-minute incubation at 37° C., 0.1 mL of proteinase K and 0.125 mL of sodium doceyl sulfate was added to the cell suspension. The cell lysate was incubated for an additional 50-minutes at 37° C. The cell lysate was extracted twice with equal volumes of phenol, twice with a 1:1 ratio of phenol/chloroform, and twice with equals of chloroform. 1/10 volume of a 3M sodium acetate solution and 2× volume of 100% ethanol were added to precipitate the DNA. The DNA was recovered by centrifugation at 16K relative centrifugal force (RCF) in an Eppendorf tabletop centrifuge (Model 5415C) for 15 minutes at 4° C. The DNA pellet was washed in 70% ethanol and air-dried; the DNA was resuspended in 10 mM Tris (pH 8.0). The DNA was stored at −20° C.

Purification of 3–5 Kilobase DNA Fragments

Four 20 $\mu$g of samples of *E. coli* W3110 chromosomal DNA were digested with 5 Units of the restriction endonuclease Sau3A. The reactions were incubated at 37° C. for 5, 10, 15, and 20 minutes, respectively. The reactions were stopped by heat inactivation of the restriction enzyme by incubation at 68° C. for 10 minutes. The DNA samples were analyzed on a 0.8% low-melting agarose gel were visualized by ethidium bromide staining. DNA fragments in the ~3–5kb size range were excised from the agarose gel (SeaPlaque Agarose, FMC BioProducts, Rockland, M.E.) and were extracted from the agarose gel using the Qiagen gel extraction kit (Qiagen, Valencia, Calif.). The DNA fragments were stored at −20° C.

Example 2

In vitro Transposition
In vitro Transposition Reactions Using a Tn5-Based Transposition System The *E. coli* W3110 DNA fragments were randomly mutagenized using the EZ::TN™<KAN-2> Insertion Kit (Epicentre Technologies, Madison, Wis.). The transposon donor DNA used in the transposition reactions was the EZ::TN™ Transposon (a linear DNA fragment), which carries the gene that confers resistance to Kanamycin between the ends of the transposable element. Per Epicentre's instructions, 0.2 μg of the target DNA (*E. coli* W3110 DNA fragments) was incubated with molar equivalents of the EZ::TN™ <KAN-2> Transposon and 1U of the EZ::TN™ <Kan2> transposase. The reaction mixture was incubated for 2 hours at 37° C. The transposition reaction was stopped by adding 1 μL of the 10× Stop Solution and incubating the mixture for 10 minutes at 70° C.

In vitro Transposition Reactions Using a Tn7-Based Transposon System

The *E. coli* W3110 DNA fragments were randomly mutagenized using the GPS™-1 Genome Priming System (New England Biolabs, Beverly, Mass.). The transposon donor plasmid used in the transposition reaction was pGPS1, which carries the gene that confers resistance to Kanamycin between the ends of the transposable element. The transposon donor plasmid pGPS1 and the target DNA (W3110 DNA fragments) were mixed in a 1:4 molar ratio, respectively and incubated with the TnsABC* transposase, which catalyzes the mobilization of the transposon from the donor DNA into a random site within the W3110 target DNA. After the transposition complexes are allowed to assemble for 10 minutes at 37° C., 1 μL of the "Start Solution" was added and the transposition reaction was incubated for an additional 60 minutes at 37° C. The reaction was stopped by heat inactivation the transposase by incubating the reaction at 75° C. for 10 minutes. The DNA was extracted once with equal volumes of a 1:1 phenol/chloroform mixture and ethanol precipitated with $\frac{1}{10}^{th}$ volume 3M sodium acetate and 2× volume of 100% ethanol. The DNA mixture was centrifuged at 16K RCF at 4° C. (Haereaus Biofuge Fresco). The DNA pellet was washed with 70% ethanol and air-dried. The DNA was resuspended in 10 mM Tris (pH 8.0).

Example 3

DNA Library Construction
Preparation of the Tn5-Based Mutant DNA Library

Sau3A digested W3110 DNA fragments (50 ng) containing the EZ::TN <Kan2 > (Tn5-based) insertions (Kanamycin-resistant) were ligated into the dephosphorylated BamHI of pTSCSE7 (50 ng). The plasmid pTSCSE7 is a derivative of temperature sensitive vector pTSC29 and contains a gene that confers resistance to Chloroamphenicol (G. J. Phillips *Plasmid* (1999) 41, 78–81). pTSCSE7 also contain the npr-sacB gene from pBE83, which confers sensitivity to sucrose (V. Nagarajan, H. Albertson, M. Chen and J. Ribbe *Gene* (1992) 114, 121–126). The ligation reactions were done according to manufacturing specifications (New England Biolabs, Beverly, Mass.) and were incubated overnight at 16° C.

Any temperature-sensitive replicon can be used in the preparation of the mutant DNA library. The vector of choice must contain a selectable marker that is different from selectable marker that is present between transposon ends.
Preparation of Tn7-Based Mutant DNA Library Sau3A digested *E. coli* W3110 DNA fragments (100 ng) containing the Transprimer transposon (Tn7-based transposon) insertions (Kanamycin-resistant) were ligated into the dephosphorylated BamH1 site of pTSA29 (60 ng), a temperature sensitive vector and also confers resistance to Ampicillin (G. J. Phillips *Plasmid* (1999) 41, 78–81). The ligation reaction was done according to manufacturing specifications (New England Biolabs, Beverly, Mass.) and was incubated overnight at 16° C.

As stated above, any temperature-sensitive replicon can serve as the vector in the preparation of the mutant DNA library. The only requirement will be that the vector contains a selectable marker that is different from that of the transposon.

Example 4

Transformation of *E. coli* and Screening for Double and Single Crossover Events
Transformation of *E. coli* W3110 (Rec+) with the Tn5-based Mutant DNA Library Electroporation competent *E. coli* W3110 (Rec$^+$) cells were transformed with 1 μL of the Tn5-based mutant DNA library. The cells recovered in SOC medium (per liter: Bacto tryptone 20 g, yeast extract 5 g, NaCl 0.584 g, KCL 0.186 g, pH to 7.0) for 60 min at 37° C. The electroporation mixture was plated onto LB agar plates (per liter: Bacto tryptone 10 g, yeast extract 5 g, NaCl 10 g) containing 30 μg/mL Kanamycin and was incubated at 30° C.

Screening for Integration Events in the Tn5-Based Mutant DNA Library: Double and Single Crossover Events Individual colonies growing on LB-Kanamycin (30 μg/mL) agar plates were inoculated into 96-well microtiter plates, each well contained 150 μL of LB broth containing 30 μg/mL Kanamycin, 0.2% glucose, 20 mM Tris-Cl (pH 8.0), and were incubated at 30° C. overnight.

Using a 96-pin Transferable Solid Phase (TSP) Screening System (Nunc, Rochester, N.Y.), culture was transferred from the "master plate" to two 96-well plates containing LB broth plus 30 μg/mL kanamycin, 0.2% glucose, 20 mM Tris-Cl (pH 8.0). One plate was incubated overnight at 30° C. and the other plate was incubated overnight at 42° C. The cultures grown at 30° C. were used for plasmid isolation; DNA sequencing of the plasmid DNA revealed the location of the Tn5 insertion within the *E. coli* W3110 DNA. The cultures grown at 42° C. were used to isolate chromosomal mutations; all cells capable of growing at 42° C. that have undergone homologous recombination that resulted in either single or double-crossover events.

Following overnight growth at 42° C., each culture was pinned using the 96-pin TSP replicator onto a LB agar plate containing 30 μg/mL kanamycin, two LB agar plates containing 30 μg/mL Kanamycin plus 5% sucrose and a LB plate containing 30 μg/mL kanamycin plus 15 μg/mL chloramphenicol. All plates were incubated overnight at 42° C. and the following day the cultures were evaluated for their ability to grow on LB-kanamycin, LB-kanamycin-sucrose) and LB-kanamycin-chloramphenicol agar plates.

Since the kanamycin-resistance marker was carried by Tn5-based transposon, all cultures were able to grow on the LB-kanamycin agar plates. A portion of the cultures contained cells that could grow on the LB-kanamycin-chloramphenicol agar plates, but could not grow on the LB-kanamycin-sucrose agar plates. This indicated that single-crossover events had occurred and that the vector DNA was integrated into the host's genome (FIG. 1). We found that some of the cultures can only exist as single-crossover events, which may suggest that the gene(s) are essential for growth under all conditions (Table 1).

There were also cultures that could grow on LB-kanamycin agar plates and the LB-kanamycin-sucrose agar plates, but not on the LB-kanamycin-chloramphenicol agar plates. This suggested that double crossover events had taken place. In double-crossover events, the transposon-disrupted gene replaces the functional chromosomal copy of the gene and the vector sequences, which contain the sacB gene, are lost.

Since homologous recombination does not occur simultaneously in every cell, cultures grown in LB-kanamycin broth generally contain cells that have undergone single-cross over events and may also contain cells that have undergone double crossover events. In order to generate a homogenous culture for each mutant (a culture in which all the cells are either in a double-crossover configuration or all the cells are in a single-crossover configuration, a "Phenotype Master Plates" was made for each 96-well plate. A 96-well plate containing ~150 μL LB broth containing 30 μg/mL Kanamycin was first inoculated with cells from the LB-kanamycin-sucrose agar plate (cells were in the double-crossover configuration). The remaining wells of the 96-well plate was filled with cells that could grow on the LB-kanamycin-chloramphenicol agar plate but could not grow on the LB-kanamycin-sucrose agar plate (cell were in the single-crossover configuration. Once each mutant was arrayed onto the "Phenotype Master Plate" in the same configuration as the original "Master Plate", the plates were incubated overnight at 42° C. The following day, an equal volume of a 50% solution of LB-glycerol was added to each well of "Phenotype Master Plate". The plate was stored at −80° C.

Validation of the "Phenotype Master Plate" Integration Status for the Tn5-based Library To confirm the integration status of each mutant, cells from the "Phenotype Master Plate" were inoculated into fresh LB broth containing 30 μg/mL kanamycin and the 96-well plate was grown overnight at 42° C. Cells were replica-pinned using a TSP replicator onto LB agar plates containing 30 1 μg/mL kanamycin, LB agar plates containing 30 μg/mL kanamycin plus 5% sucrose, and LB agar plates containing 30 μg/mL kanamycin plus 15 μg/mL chloramphenicol. It was found that >98% of the cultures were correctly identified (FIG. 2). The "Phenotype Master Plates" can be further analyzed using high-throughput phenotypic screens.

Transformation of E. coli W3110 (Rec+) with the "Tn7-based" Mutant DNA Library

Electroporation competent E. coli W3110 (Rec+) cells were transformed with 1 μL of the Tn7-based library DNA. The cells recovered in SOC medium (per liter: Bacto tryptone 20 g, yeast extract 5 g, NaCl 0.584 g, KCL 0.186 g, pH to 7.0) for 60 min at 37° C. The electroporation mixture was plated onto LB plates (per liter: Bacto tryptone 10 g, yeast extract 5 g, NaCl 10 g) containing 15 μg/mL kanamycin and the plates were incubated at 42° C.

Screening for Integration Events in The Tn7-based Mutant DNA Library: Double and Single Crossover Events Individual colonies grown on LB-kanamycin plates were inoculated into 96-well microtiter plates, each well contained 200 μL LB broth plus 15 μg/mL Kanamycin, 0.2% glucose, 20 mM Tris-Cl (pH 8.0), and were incubated at 42° C. overnight with aeration.

Using a 96-well pin replicator, ~1–2 μL of culture from the "master plate" was used to inoculate a new 96-well plate containing only LB broth. The cultures were grown overnight with aeration. Four 100-fold serial dilutions were made into fresh LB medium, i.e. ~1–2 μL of the LB culture was inoculated into 200 μL of fresh LB broth.

Following growth overnight at 42° C. with aeration, the diluted cultures were pin replicated onto LB agar plates plus 15 μg/mL kanamycin (marker present on transposon) and LB agar plates containing 15 μg/mL kanamycin and 25 μg/mL ampicillin (marker present on vector). The LB agar plates were incubated overnight at 42° C. and the following day the LB-kanamycin agar plates and the LB-kanamycin-ampicillin agar plates were evaluated for growth.

As expected, it was observed that all cultures could grow on the LB-kanamycin agar plate (FIG. 3). However, only a portion of the cultures could grow on the LB-kanamycin-ampicillin agar plate. This growth indicated that single crossover events had occurred and that the entire plasmid was integrated into the host's genome (FIG. 3). Some of the cultures can only exist as single-crossover events, which may suggest that the gene(s) are essential for growth under all condition.

A portion of the cultures was able to grow on the LB-kanamycin agar plates, but was unable to grow on the LB-kanamycin-ampicillin agar plates. This suggested that double crossover events had taken place in these cultures (FIG. 3); the transposon-disrupted gene has replaced the functional chromosomal copy of the gene and the vector sequences were lost.

Example 5

Identification Mutant Phenotypes

All 96 mutants from each "Phenotype Master Plate" were evaluated to determine their phenotype by inoculating liquid or solid medium containing various substrates of interest. For example, the "Phenotype Master Plates" was evaluated for the presence of auxotrophs, i.e., transposon-generated mutants that are unable to synthesize all 20 amino acids that are essential for growth on minimal (M9) medium. Mutants containing auxotrophic mutations were identified by replica pinning cultures from the "Master Plate" (mutants were grown in LB broth plus 30 μg/mL Kanamycin) onto M9 agar plates (per liter: 6 g $Na_2HPO_4 \cdot H_2O$, 3 g $KH_2PO_4$, 0.5 g NaCl, 1 g $NH_4Cl$, supplemented with 1 mL of 1M $MgSO_4$, 1 mL 0.1M $CaCl_2$, 15 μg/mL Kanamycin, and 15 g Bacto agar). Since M9 is minimal nutrient medium, mutants unable to synthesize their own amino acids could not grow on the M9 agar plates. Thus, auxotrophic mutants could easily be identified my pinning onto M9 agar plates (FIG. 4a and FIG. 4b).

Colorimetric assays were also used to screen the transposon-tagged mutants. Phenol red broth (10 g/L proteose peptone, 1 g/L beef extract, 5 g/L sodium chloride, 0.018 g/L phenol red) supplemented with various sugars (glucose, maltose, sucrose, lactose, and glycerol.) was used to screen the "Phenotype Master Plates" for the mutants that were altered in their ability to produce acid when the sugar substrate is metabolized. 100 μL of phenol red broth containing various sugars (for example, maltose and sucrose) was inoculated using a 96-pin TSP replicator with cultures grown in LB broth containing 30 μg/mL Kanamycin. The microtiter plates were incubated overnight at 42° C. and the following day the microtiter plates were screened for color changes. Phenol red is a pH indicator that is red at neutral pH, yellow at acidic pH and fuchsia at basic pH.

The wild-type E. coli W3110 strain is able to produce acid when grown in the presence of maltose. Using this screen, a mutant was identified that was unable to produce acid when grown in phenol red broth supplemented with maltose (FIG. 5a). The location of the Tn5 insertion was identified using single primer PCR and DNA sequencing. It was found that the Tn5-based transposon was inserted within the malK gene. The role of malK gene product (MalK) is to transport maltose into the cell. Since the Tn5-based transposon had interfered with the ability of MalK mutant to transport maltose into the cell, there was no acid produced and the pH of the culture remains neutral.

The wild-type E. coli W3110 strain is not able to produce acid when grown in the presence of sucrose. The pH of the phenol red broth containing sucrose remains neutral and the color of the broth is red as indicated by the phenol pH indicator.

Colorimetric assays may also be use to screen for gain-of-function mutations, in addition to the traditional loss-of-function mutations. Transposon-tagged mutants were identified that had acquired the ability to produce acid when grow in the presence of sucrose (FIG. 5b). The location of the Tn5 insertions were determined using single primer PCR and DNA sequencing. The Tn5-based transposon was found to be inserted within the unknown genes ycfW and yceA, and a gene, betB, involved in glycine betaine synthesis from choline. The roles of the transposon-disrupted ycfW, yceA and betB gene products in the production of acid when cell are grown in sucrose medium will be further analyzed.

Identification of Essential Genes for Growth

All cells contain genes that are essential for growth under all conditions. For this class of essential genes, cells that have undergone double-crossover events can never be obtained, because the replacement of an intact gene with a transposon-disrupted gene is a lethal event. Comparing their integration frequency with cultures known to have undergone gene replacement can identify these essential mutations. Cultures containing mutation in essential genes will have an integration frequency that is significantly lower than the integration frequency of cultures containing mutation in non-essential genes.

An assay was developed that permited the rapid identification of genes that are essential for growth in complex medium (LB). Screening for integration events (single or double crossover events), cultures were identified that were unable to grow on LB agar plates containing 30 µg/mL kanamycin plus 5% sucrose. These cultures appeared to contain cells that could only exist in the single crossover configuration, which suggested that the Tn5-based transposon had inserted into a gene that was essential for growth in complex (LB) medium. These "single-crossover" cultures were further evaluated for their ability to grow on LB agar plates containing 30 µg/mL kanamycin plus 5% sucrose.

The "single-crossover" cultures were inoculated into 5 mL of LB broth containing 30 µg/mL Kanamycin and were grown overnight at 30° C. with aeration (~250 RPM) in a shaking environmental chamber (Orbit Environ Shaker). A 1:1000 dilution was made into 5 mL of LB broth and the cultures were grown overnight at 42° C. with aeration (~250 RPM). The following day, 100-fold dilutions were made of each culture. 100 µL of the $10^{-2}$, $10^{-6}$ and $10^{-8}$ dilutions were plated in duplicate using sterile glass beads onto LB agar plates containing 30 µg/mL Kanamycin, LB agar plates containing 30 µg/mL Kanamycin plus 5% sucrose and LB agar plates containing 30 µg/mL kanamycin plus 15 µg/mL chloramphenicol. The colony forming units (CFU)/mL was determined for each culture. Examples of mutants found to be essential for growth in complex medium using the described assay are shown in Table 1. It was observed that the three 'single-crossover" mutants evaluated were only able to exist in the single crossover configuration and exhibited growth features that were similar to the "single-crossover" controls murA(Z) and ispB (two genes that are known to be essential for growth in E. coli). Thus, it is likely that these unknown genes (ycfW, yijT and torT) are also essential for growth of E. coli W3110.

An assay was also developed that permits the identification of a class of mutations known dominant lethals. This class of mutations can not be isolated as single-crossover events, as described above, because these mutations are lethal even though there is an intact copy of the gene present in the cell. The use of a temperature sensitive vector was important in the identification of the dominant lethal mutations.

The E. coli W3110 chromosomal DNA fragments were disrupted by the Tn7-based transposon, ligated into a temperature-sensitive vector (pTSA29), and the DNA plasmids were introduced into the cells via electroporation. The transformation mixture was plated onto LB agar plates containing 15 µg/mL kanamycin and incubated overnight at 30° C. Sixteen colonies for each mutant were inoculated in a 96-well microtiter plate and was grown overnight at 30° C. with aeration in 200 µL of LB broth containing 15 µg/mL Kanamycin. The 96-well replica pins were used to make 100-fold serial dilutions ($10^{-2}$,$10^{-4}$,$10^{-6}$,$10^{-8}$) of the cultures into 200 µL of LB broth containing 15 µg/mL kanamycin; the replica pins were dipped into ethanol and flamed to sterilize between each dilution series. Two sets of cultures were generated; one set of diluted cultures was incubated overnight at 30° C. with aeration and the other set of diluted cultures was incubated overnight at 42° C. with aeration. The optical density (Abs$^{600}$)was determined for each plate using a BioAssay Reader (HTS7000 Plus, Perkin Elmer, Norfolk, Conn.). The plates were also pinned onto LB agar plates contain 15 µg/mL kanamycin and were incubated overnight at 30° C. or 42° C., respectively. It was observed that all mutants were able to grow at 30° C., some mutants were unable to grow at 42° C. This result was independent of whether the cultures were grown in liquid or on solid medium. The inability of cells to grow at the 42° C. would suggest that the transposon might have disrupted an essential gene for growth under the specific condition. Since the cells could not exist in a single crossover configuration, the phenotype of the transposon-disrupted gene may exhibit dominance over the phenotype of the intact gene (FIG. 6).

TABLE 1

Screen for Essential Genes ("Stable" Single Cross-Over Events)

| Transposon Mutants | Medium | | |
| --- | --- | --- | --- |
| | kanamycin (CFU/mL) | kanamycin/ chloramphenicol (CFU/mL) | kanamycin/ sucrose (CFU/mL) |
| murA (Single)[a] | 5 × 10$^8$ | 3.2 × 10$^8$ | <1 |
| IspA (Single)[a] | 7.2 × 10$^8$ | 7.3 × 10$^8$ | <1 |
| MalK (Double)[a] | 2.3 × 10$^9$ | <1 | 2.6 × 10$^9$ |
| ycfW | 1.4 × 10$^9$ | 8 × 10$^8$ | <1 |
| yijI | 1.2 × 10$^9$ | 9 × 10$^8$ | <1 |
| torT | 5.8 × 10$^8$ | 7 × 10$^7$ | <1 |

[a]controls

Example 6

Identification of the Transposon Insertion Site within the E. coli W3110 DNA

The location of the insertion of the transposon into the W3110 chromosomal DNA library was identified by sequencing plasmid DNA, or by sequencing PCR products. To isolate plasmid DNA for DNA sequencing, eight Qiagen "24-well blocks RB" were used to grow 10 mL cultures in LB broth supplemented with 30 μg/mLKanamycin, 0.2% glucose, 20 mM Tris-Cl (pH 8.0). 10 μL of cells from the "Master Plates" were the source of inoculum. The cultures were grown overnight at 30° C. at ~300 RPM on a shaking platform (Ika-Schuttler Mts4) and were harvested by centrifugation for at 4° C. 10 minutes at 4 K g in a Sorvall Super T21 tabletop centrifuge (PN11779 swing bucket rotor). The plasmid DNA was extracted using the Qiagen "QIAprep 96 Turbo Miniprep Kit". The plasmid DNA was electrophoresed through a 0.8% agarose gel and visualized by illumination of the ethidium bromide stained gel. The purified plasmid DNA was submitted for sequencing at a DNA sequencing facility that uses an Applied Biosystem (ABI) DNA sequencer. The site of the transposon insertion was determined by using DNA sequencing primers that are homologous to the ends of the transposon. For sequencing the Tn5-based transposon insertions, the following DNA sequencing primers were used: KAN-2RP-1 (5'GCAATGTAACATCAGAGATTTTGAG3':SEQID NO:1) and KAN-2FP-1 (5'ACCTACAACAAAGCTCTCATCAACC3':SEQID NO:2). For sequencing the Tn7-based transposon insertions, the following DNA sequencing primers were used: Tn7L.SEQ (5'ATCCTTAAAAACTCCATTTCCACCCCT3':SEQID NO:5) and Tn7R.SEQ (5'ACTTTATTGTCATAGTTTAGATCTATTTTG3'SEQID NO:6)

Transposon insertion sites were also determined a single-primer PCR method (Karlyshev, A. V. et al. BioTechniques (Natick, Mass.) (2000), 28(6), 1078–1082). Cells from the "Phenotype Master Plate" were mixed 1::3 with 10 mM Tris-EDTA (TE) buffer and were boiled for 5 minutes in an ABI 9600 Thermocycler. The cellular debris was pelleted by centrifugation for 10 minutes at 4° C. at 4 K g in the Sorvall Super T21 tabletop centrifuge (PN11779 swing bucket rotor). The standard PCR reactions were either 50 μL or 100 μL to which 5–15 μL of boil cell lyste and 1 μL of primer (45–60 pmol) was added. One of two PCR primers (KAN-2RP-PCR: 5'TTGGAATTTAATCGCGGCCTCGAGC3' (SEQID NO:3) or KAN-2FP-PCR: 5'GACGGCG-GCTTTGTTGAATAAATCG3' (SEQID NO:4)) were used to amplify the region that the Tn5-based transposon had inserted into the E. coli W3110 chromosomal DNA. For the genes disrupted by the Tn7-based transposon, two primers (Tn7L.PCR::5'CCAACCAGATAAGTGAAATCTAGTTCC3' (SEQID NO:7) and Tn7R.PCR: 5'CCCTCTTTAATAC-GACGGGCAATT GC3'(SEQID NO:8)) were designed to amplify the insertion site of the Tn7-based transposon. The PCR amplification was performed in five steps with three sets of cycles using the ABI 9600 Thermocycler. The five steps were the following: 1) 94° C., 5 minutes; 2) 20 cycles (94° C., 30 seconds; 60° C., 30 seconds; 72° C., 3 minutes); 3) 30 cycles (94° C., 30 seconds; 40° C., 30 seconds; 72° C., 2 minutes); 4) 30 cycles (94° C., 30 seconds; 60° C., 30 seconds; 72° C., 2 minutes); 5) 72° C., 7 minutes. 10 μL of the PCR products were electrophoresed on a 0.8% agarose gel; the DNA fragments were visualized by ethidium bromide staining and UV illumination. The remaining 90 μL of each reaction was cleaned up and prepared for DNA sequencing using the QIAquick 96 PCR Purification Kit. The PCR products were sequenced using the DNA sequencing primer sets described above. The Tn5-based transposon PCR products were sequenced using PCR primers KAN-2RP-PCR: 5'TTGGAATTTAATCGCGGCCTCGAGC3' (SEQID NO:3) or KAN-2FP-PCR: 5'GACGGCGGCTTTGTTGAATAAATCG3'(SEQID NO:4). The Tn7-based transposon PCR products were sequenced using PCR primers Tn7L.PCR::5'CCAACCAGATAAGTGAAATCTAGTTCC3 '(SEQID NO:7) and Tn7R.PCR: 5'CCCTCTTTAATAC-GACGGGCAATT GC3'(SEQID NO:8). The location of the transposon insertion into the E. coli W3110 DNA was determined by comparing the sequence of the PCR sample by BLAST analysis to the E. coli genomic sequence within National Center for Biotechnology Information database (NCBI).

Example 7

Creation of Rhodococcus Mutants

Preparation of AN12 Chromosomal DNA

Rhodococcus erythropolis AN12 was grown in 25 mL NBYE medium (0.8% nutrient broth, 0.5% yeast extract, 0.05% Tween 80) till mid-log phase at 37° C. with aeration. Bacterial cells were centrifuged at 4,000 g for 30 min at 4° C. The cell pellet was washed once with 20 mL of 50 mM $Na_2CO_3$ containing 1 M KCl (pH 10) and then with 20 mL of 50 mM NaOAc (pH 5). The cell pellet was gently resuspended in 5 mL of 50 mM Tris-10mM EDTA (pH 8) and lysozyme was added to a final concentration of 2 mg/mL. The suspension was incubated at 37° C. for 2 h. Sodium dodecyl sulfate was then added to a final concentration of 1% and proteinase K was added to 100 μg/mL final concentration. The suspension was incubated at 55° C. for 5 h. The suspension became clear. The clear lysate was extracted with equal volume of phenol:chloroform:isoamyl alcohol (25:24:1). After centrifuging at 17,000 g for 20 min, the aqueous phase was carefully removed and transferred to a new tube. Two volumes of ethanol were added and the DNA was gently spooled with a sealed glass Pasteur pipet. The DNA was dipped into a tube containing 70% ethanol, then air-dried. After air drying, DNA was resuspended in 400 μl of TE (10 mMTris-1 mM EDTA, pH 8) with RNaseA (100 μg/mL) and stored at 4° C.

Partial Restriction Enzyme Digestion of AN12 Chromosomal DNA

AN12 chromosomal DNA was used for a series of restriction digests. EcoRV, FspI, HincII, HpaI, MscI, PmlI, SspI and StuI were used to create an array of restriction digests by making all possible combinations of single and double digests. An 8×8 tube PCR reaction plate was used for the reactions. A dilution of each restriction enzyme was added to a specific column and row. Each reaction tube ended up with 0.5 μL of each enzyme (~2–4 units) for a double digest or 1.0 μL of a single enzyme. A dilution of AN12 chromosomal DNA was added so that each reaction contained approximately 200 ng of DNA. The 10×Promega Multi-Core buffer was used for all reactions and dilutions. Final reaction volume was 30 μL. The reaction was placed at 37° C. for 30 minutes. The reactions were then placed at 65° C. for 15 minutes and then combined. The combined reaction was then stored at −20° C.

Isolation of Size-Selected DNA Fragments

Two agarose gels were run, each with 90 μL of the partially digested chromosomal DNA. The DNA was size-selected by cutting out the fragments in the 2 to 6 kb range. The DNA was eluted out of the gel using the QIAquick Gel Extraction Kit from Qiagen (Valencia, Calif.), catalog 28704 using manufacturer's directions. The resulting DNA was concentrated using 3M sodium acetate and 2.5 volumes cold EtOH. The DNA was resuspended finally in a volume of 20 μL sterile water, and the concentration determined to be 50 ng/μL.

Transposition Reaction

A transposition reaction was carried out on the highly concentrated, gel purified DNA. This was done using the EZ::TN™<TET-1> Insertion Kit from Epicenter Technologies(Madison, Wis.), catalog number EZI921T. The instructions for setting up and carrying out the reaction were precisely followed. Completed reactions were stored at −20° C.

Ligation and Transformation

15 μL sterile water was added to ½ the transposition reaction, 5.5 μL. Then this diluted reaction aliquot was added to a tube of Ready-To-Go pUC18 SmaI/BAP+Ligase from Amersham Pharmacia Biotech Inc. (Piscataway, N.J.), (27-5266-01). The tube was allowed to incubate at room temperature as indicated by the Ready-To-Go instructions. Different volumes of the ligation mix were transformed into chemically competent Maximum Efficiency DH5α cells provided by Life Technologies, (#18258-012, Rockville, Md.). During outgrowth, 400 μL SOB (Maniatis, supra) media was added per reaction, and the outgrowth was kept short, 20 min at 37° C. in a rotary drum. The samples were plated onto LB+Tetracycline (10 μg/mL) plates, and allowed to incubate overnight at 37° C. The results of this transformation were good, yeilding a dozen plates with 100 to 300 colonies per plate, depending on the volume of ligation mix transformed. Colonies were picked, and placed into 96 well microtiter plates with LB+Tetracycline(10 μg/mL) and allowed to grow overnight at 37° C. on a plate shaker with an air pore cover. These plates constituted "Master Plates" or "Master phenotype plates".

Sequencing Potential Mutants in E. coli

One of the master plates was started for 96 well block miniprep growth. This growth was processed using the QIAprep Turbo Miniprep Kit from Qiagen, catalog 27191. Instructions for inoculation and processing were followed precisely as indicated in the Qiagen instruction manual. The DNA concentration of the 96 minipreps was checked by running random well aliquots on a gel. The DNA was determined to be of a good enough quality for sequencing. The primers used for sequencing were suggested by the EZ::TN™<TET-1>Insertion Kit instruction manual, and would read out from the transposon insertion. The primers used were designated as TP1, GGGTGCGCATGATCCTCTAGAGT (SEQID NO:9), and TP2, TAAATTGCACTGAAATCTAGAAATA (SEQID NO:10). The 96 well plate of miniprep DNA was sequenced using these primers. Sequencing results were analyzed and potential transposition mutants were identified. These potential mutants were processed to again make miniprep DNA, but individually, to provide a higher concentration and improved quality. This was done using the QIAprep Spin Miniprep Kit from Qiagen, catalog 27106.

Sequence analysis showed that 11 clones had inserts of significant size (over 250 bp), good quality, and homology to the Rhodococcus erythopolis genome. Four or these clones designated as, C9, E12, G4 and H8 were used for further characterization.

Electroporation Back Into ATCC47072

Rhodococcus erythropolis strain ATCC47072 was streaked onto a fresh LB plate and incubated at 28° C. for 2 days. The media used to grow ATCC47072 for electroporation was Modified S12+10 mM Citrate+0.05% Tween 80 (S12 medium, per 100 mL:1 mL of 1M ammonium sulfate, 5 mL of 1 M potassium phosphate (pH7.0), 1 mL of S10 metal mix (final concentration 200 mM $MgCl_2$, 70 mM $CaCl_2$, 5 mM $MnCl_2$, 100 μM $ZnCl_2$, 500 μM $FeCl_2$ 200 μM, thiamine hydrochloride, 172 μM $CuSO_4$, 252.4 μM $CoCl_2$, 241.9 μM $NaMoO_2$), 2 mL of 0.5 M sodium citrate, 0.05 mL of Tween80). ATCC 47072 was started for growth and was allowed to incubate in a 30° C. shaking water bath. After several hours, the culture was diluted to OD600 of 0.1, and allowed to continue to grow overnight. The next day the culture was diluted to an initial OD600 which was around 0.15. The culture was grown for 4 to 5 hours to reach OD600 of approximately 0.6. The cells were spun down at 4° C., washed 3 times with ice cold sterile water, and resuspended in a small final volume, around 1 to 2 mL, in ice cold sterile water. For the electroporation, ~1 μg of DNA was used. In a cold microfuge tube on ice, 75 μL of the concentrated cells were gently mixed with 12 to 15 μL of the miniprep DNA from clones C9, E12, G4 and H8. The mixture was then transferred to a cold electroporation cuvet. These cuvets with 1 mM gap and a 1.2–2.4 kV field strength was used. The electroporation event was performed using the Gene Pulser II System from Bio-Rad (Hercules, Calif.), catalog 165-2105. After the electroporation, the culture mix was transferred to a culture tube, and 500 μL NBYE was added. The tubes were allowed to incubate overnight in a rotary drum at room temperature. After the incubation, the cultures were plated on LB+Tetracycline (10 μg/mL) plates and placed at 30° C. Tetracycline resistant transformants appeared after 3 to 4 days.

TABLE 2

Results Of ATCC47072 Electroporation

| Clone | Number of Transformants | Comments |
| --- | --- | --- |
| C9 | ~1000 | very small (pinhead) size colonies |
| E12 | ~100 | very small (pinhead) size colonies |
| G4 | ~50 | very small (pinhead) size colonies |
| H8 | ~60 | 2 larger colonies which came up quickly Rest were very small (pinhead) size colonies |

Multiple colonies (4 to 8) were patched onto LB+tetracycline plate for each clone. A few of the colonies that had grown were further processes. These were designated as C9-1, C9-3, C9-4 and C9-8; E12-1, E12-2 E12-6 and E12-7; G4-1 and G4-2; H8-1 H8-2, H8-3, H8-5 and H8-7.

Verification of Integration by PCR

In order to verify the integration of the transposon mutant, primers were made which would amplify different regions of the transposon. Primers TP3 (SEQID NO:11) and TP4 (SEQID NO:12) were designed as reverse compliments to the two primers used for sequencing, TP1 and TP2. These will amplify most of the transposon. Primers were also designed, TP5 (SEQID NO:13) and TP6 (SEQID NO:14), that would amplify only the tetracycline resistance gene. The sequence of the transposon was supplied in the EZ::TN™<TET1> Insertion Kit instruction manual.

Lysates were made of the potential mutants in Rhodococcus using the Mini-Bead Beater 8 from Biospec Products, catalog 693. An approximate volume of 200 to 250 μL of bead beater beads was added to bead beater vials. The bead beater beads were 0.1 mM zirconia/silica beads from Biospec Products (Bartlesville, Okla.), catalog 11079101. 300 μL cell lysis buffer (20 mM Tris, pH 8.0, 2 mM EDTA, 1% Triton X-100) was added to each vial. A large loopful of cells was added to each vial. The vials were then placed in the Mini-Bead Beater 8. The vials were "beaten" for 2 minutes on the homogenize setting. 100 μL sterile water was added to each vial. Vials were spun in a microcentrifuge 2 times for 10 minutes to remove the beads. The lysate was then moved to a sterile microcentrifuge tube. The lysate was then diluted with water, in the range of 1:2.5 to 1:5, depending on the amount of cells added initially to the vial. This diluted lysate was then used as the template in PCR reactions. Five μL of lysate was used in a reaction of a final volume of 100 μL. PCR reactions were setup using the two primer sets described above, TP3 with TP4, and TP5 with TP6. The sequence of each primer is as follows:

TP3-TATTTCTAGATTTCAGTGCAATTTA (SEQ ID NO:11),

TP4-ACTCTAGAGGATCATGCGCACCC (SEQ ID NO:12),

TP5-ATGAAATCTAACAATGCGCT (SEQ ID NO:13)

and

TP6-ATTCAGGTCGAGGTGGCCCG (SEQ ID NO:14).

The PCR was set up using the following parameters for 40 cycles: denaturation at 94° C. for one minute, annealing at 55° C. for one minute and extension at 72° C. for one minute. Standard agarose gel analysis was performed and the presence of the following PCR fragments was demonstrated. The TP5 and TP6 primers, which were designed to amplify the tetracycline resistance region of the transposon and give a PCR product of 1192 bp in size, worked for the following clones, C9-3, G4-1, G4-2, H8-1, H8-2, H8-3, H8-5 and H8-7. The TP3 and TP4 primers, which were designed to amplify most of the region of the EZ::TN™<TET1> transposon and give a PCR product of 1545 bp, worked for the following clones, C9-3, G4-2, H8-1, H8-2, H8-5 and H8-7. The formation of these PCR products indicates the presence of the transposon in Rhodococcus, showing integration has occurred. In the case clone G4 and H8, all the colonies were positive for the tetracycline gene. However, in the case of C9, only one of the colonies was positive for tetracycline. It is not clear whether it was due to lack of integration of due to PCR conditions. Patches from clone E12 did not give PCR products using either primer set.

The results show that gene disruption can be obtained in *Rhodococcus erythropolis*.

What is claimed is:

1. A method for the identification of an essential gene responsible for the presence of a specific phenotype on a recombination proficient microorganism comprising:
   a) contacting In vitro:
      (i) a transposable element comprising at least one first genetic marker;
      (ii) a transposase for the insertion of the transposable element into the essential gene; and
      (iii) a target DNA containing the essential gene, said gene having a homolog in the genome of the recombination proficient microorganism;
   under suitable conditions whereby the transposable element inserts within the essential gene to form a transposon disrupted gene;
   b) cloning the transposon disrupted gene into a suitable vector to form a chromosomal integration vector, said vector comprising at least one second genetic marker;
   c) transforming a recombination proficient microorganism which is not naturally transformable with the chromosomal integration vector of step (b) to create at least one transformant;
   d) selecting the at least one transformant of step (c) under conditions whereby no chromosomal integration occurs between the chromosomal integration vector and the genome of the transformant, by identifying transformants expressing the first genetic marker;
   e) culturing the identified transformants of step (d) under conditions whereby chromosomal integration occurs between the chromosomal integration vector and the genome of the transformant;
   f) selecting transformants of step (e) which express either the first genetic marker or both the first and second genetic markers by which transformants having undergone either a single or double crossover event are identified;

g) screening the transformants of step (f) which have undergone either a single or double crossover event, for the presence of a specific phenotype wherein the transformants which are positive for the specific phenotype contain a transposon disrupted gene; and h) isolating the transposon disrupted gene from the transformant of step (g) which is positive for the specific phenotype.

2. A method according to claim 1 wherein step (d) is optionally deleted.

3. A method according to claim 1 wherein after step (h) the isolated gene is optionally sequenced.

4. A method according to claim 1 wherein said target DNA is restricted chromosomal DNA.

5. A method according to claim 1 wherein said target DNA is an isolated DNA fragment.

6. A method according to claim 1 wherein said at least one first genetic marker and said at least one second genetic marker are different.

7. A method according to claim 6 wherein the at least one second genetic marker is selected from the group consisting of the SacB gene and a gene encoding Tetracycline resistance.

8. A method according to claim 1 wherein the genetic markers are selected from the group consisting of antibiotic resistance markers, metal resistance markers, substrate-utilization markers, and genes encoding fluorescent and bioluminescent proteins.

9. A method according to claim 1 wherein said chromosomal integration vector is a temperature sensitive vector which integrates into a host genome at a permissive temperature.

10. A method according to claim 1 wherein the recombination proficient microorganism is selected from the group consisting of bacteria, yeast and filamentous fungi.

11. A method according to claim 10 wherein the recombination proficient microorganism is selected from the group consisting of Pseudomonas, Bacillus, Bacteriodes, Vibrio, Yersinia, Clostridium, Mycobacterium, Mycoplasma, Coryynebacterium, Escherichia, Salmonella, Shigella, Rhodococcus, Methanococcus, Streptomyces, Arthrobacter, Listeria, Klebsiella, Aeromonas, Xanthomonas, Aspergillus, Trichoderma, Saccharomyces, Pichia, Candida, and Hansenula.

12. A method according to claim 1 wherein the specific phenotype is selected from the group consisting of cell growth, enzymatic activity, metabolic capacity, resistance to inorganic chemicals, resistance to organic chemicals, resistance to biological chemicals, resistance to biological agents, resistance to physical extremes, fatty acid composition, degradation, and hydrolysis.

13. A method according to claim 1 wherein the specific phenotype may be detected by growth on selective media, by enzyme assay or metabolic assays.

14. A method according to claim 1 wherein immediately following either step (b), (c) or (d) the transposon disrupted gene is isolated and sequenced.

15. A method according to claim 1 wherein after step (f) the transformants of step (f) are optionally re-selected for those transformants which express either the first marker or both the first and second markers.

16. A method for the identification of an essential gene responsible for the cell growth under any condition in a recombination proficient microorganism comprising:

a) contacting In vitro
   (i) a transposable element comprising at least one marker;
   (ii) a transposase for the insertion of the transposable element into the essential gene; and
   (iii) target DNA containing the essential gene, said gene having a homolog in the genome of the recombination proficient microorganism;

under suitable conditions whereby the transposable element inserts within the essential gene to form a transposon disrupted gene;

b) cloning the transposon disrupted gene into a temperature sensitive vector containing a second genetic marker to form a temperature sensitive chromosomal integration vector;

c) transforming a recombination proficient microorganism, which is not naturally transformable, with the temperature sensitive chromosomal integration vector of step (b) to create at least one transformant;

d) culturing the at least one transformant of step (c) at a permissive temperature whereby no chromosomal integration occurs between the chromosomal integration vector and the genome of the transformant;

e) identifying transformants of step (d) expressing the marker;

f) culturing the identified transformants of step (e) at non-permissive temperatures whereby chromosomal integration occurs between the chromosomal integration vector and the genome of the transformant;

g) selecting transformants of step (e) which did not grow at step (f) after chromosomal integration between the chromosomal integration vector and the genome of the transformant and which contain a transposon disrupted gene; and h) isolating the transposon disrupted gene from the transformant of step (g) which is responsible for cell growth under any condition.

17. A method according to claim 16 wherein after step (h) the isolated gene is optionally sequenced.

18. A method according to claim 16 wherein said target DNA is restricted chromosomal DNA.

19. A method according to claim 16 wherein said target DNA is an isolated DNA fragment.

20. A method according to claim 16 wherein said at least one first genetic marker and said at least one second genetic marker are different.

21. A method according to claim 16 wherein the recombination proficient microorganism is selected from the group consisting of bacteria, yeast and filamentous fungi.

22. A method according to claim 21 wherein the recombination proficient microorganism is selected from the group consisting of Pseudomonas, Bacillus, Bacteriodes, Vibrio, Yersinia, Clostridium, Mycobacterium, Mycoplasma, Coryynebacterium, Escherichia, Salmonella, Shigella, Rhodococcos, Methanococcus, Streptomyces, Arthrobacter, Listeria, Klebsiella, Aeromonas, Xanthomonas, Aspergillus, Trichoderma, Saccharomyces, Pichia, Candida, and Hansenula.

23. A method for the identification of an essential gene responsible for the presence of a specific phenotype in a recombination proficient microorganism comprising:

a) contacting In vitro:
   (i) a transposable element comprising at least one first marker;
   (ii) a transposase for the insertion of the transposable element into the essential gene; and
   (iii) target DNA containing the essential gene, said gene having a homolog in the genome of the recombination proficient microorganism;

under suitable conditions whereby the transposable element inserts within the essential gene to form a transposon disrupted gene;
- b) cloning the transposon disrupted gene into a suitable vector to form a chromosomal integration vector, said vector comprising at least one second marker and at least one third marker;
- c) transforming a recombination proficient microorganism which, is not naturally transformable, with the chromosomal integration vector of step (b) to create transformants;
- d) selecting the transformants of step (c) under conditions whereby no chromosomal integration occurs between the chromosomal integration vector and the genome of the transformant, by identifying transformants expressing the first marker;
- e) culturing the identified transformants of step (d) under conditions whereby chromosomal integration occurs between the chromosomal integration vector and the genome of the transformant;
- f) selecting transformants of step (e) which express either the first marker alone, the first and second markers alone, or the first, second and third markers, by which transformants having undergone either a single or double crossover event are identified;
- g) screening the transformants of step (f) which have undergone either a single or double crossover event, for the presence of a specific phenotype wherein the transformants which are positive for the specific phenotype contain a transposon disrupted gene; and
- h) isolating the transposon disrupted gene from the transformant of step (g) having the specific phenotype.

24. A method according to claim 23 wherein after step (h) the isolated gene is optionally sequenced.

25. A method according to claim 23 wherein said target DNA is restricted chromosomal DNA.

26. A method according to claim 23 wherein said target DNA is an isolated DNA fragment.

27. A method according to claim 23 wherein said third marker is the sacB gene.

28. A method according to claim 23 wherein the recombination proficient microorganism is selected from the group consisting of bacteria, yeast and filamentous fungi.

29. A method according to claim 28 wherein the recombination proficient microorganism is selected from the group consisting of Pseudomonas, Bacillus, Bacteriodes, Vibrio, Yersinia, Clostridium, Mycobacterium, Mycoplasma, Coryynebacterium, Escherichia, Salmonella, Shigella, Rhodococcus, Methanococcus, Streptomyces, Arthrobacter, Listeria, Klebsiella, Aeromonas, Xanthomonas, Aspergillus, Trichoderma, Saccharomyces, Pichia, Candida, and Hansenula.

30. A method according to any one of claim 1, 16 or 23 wherein the target DNA is a suitable vector which is contacted with the transposable element and the transposase under suitable conditions whereby the transposable element inserts within the essential gene to form a chromosomal integration vector, and whereby step (b) is deleted.

31. A method according to claim 30 wherein the chromosomal integration vector comprises at least one second genetic marker.

32. A method according to any one of claim 1, 16 or 23 wherein the transposon is selected from the group consisting of, those based upon the yeast Ty1 element, those based upon the bacterial transposon Tn7, the EZ::TN, those based on the bacteriophage Mu, those based on the bacterial transposon Tn552, and the mariner transposable element Himar1.

33. A method according to claim 1 wherein the genetic markers are selected from the group consisting of lacZ, gfp, cat, galK, inaZ, luc, luxAB, bgaB, nptII, phoA, uidA and xylE.

34. A method according to either of claims 7 or 27 wherein the sacB gene is npr-sacB.

* * * * *